US010184941B2

(12) United States Patent
Banks et al.

(10) Patent No.: US 10,184,941 B2
(45) Date of Patent: Jan. 22, 2019

(54) USE OF ACY-1 AS A MARKER OF ISCHAEMIA/REPERFUSION, DELAYED GRAFT FUNCTION AND GRAFT VIABILITY AS WELL AS METHOD THEREOF

(71) Applicant: University of Leeds, Leeds, Yorkshire (GB)

(72) Inventors: Rosamonde Elizabeth Banks, Leeds (GB); Matthew Peter Welberry Smith, Leeds (GB); Peter John Selby, Leeds (GB); Andrew Lewington, Leeds (GB)

(73) Assignee: University of Leeds, Leeds, Yorkshire (GB)

(*) Notice: Subject to any disclaimer, the term of this patent is extended or adjusted under 35 U.S.C. 154(b) by 125 days.

(21) Appl. No.: 14/775,219

(22) PCT Filed: Mar. 13, 2014

(86) PCT No.: PCT/GB2014/050768
§ 371 (c)(1),
(2) Date: Sep. 11, 2015

(87) PCT Pub. No.: WO2014/140595
PCT Pub. Date: Sep. 18, 2014

(65) Prior Publication Data
US 2016/0033507 A1    Feb. 4, 2016

(30) Foreign Application Priority Data

Mar. 13, 2013    (GB) .................................. 1304460.7

(51) Int. Cl.
| | |
|---|---|
| G01N 33/68 | (2006.01) |
| G01N 33/577 | (2006.01) |
| G01N 33/563 | (2006.01) |
| G01N 33/573 | (2006.01) |
| C12N 9/80 | (2006.01) |
| C12Q 1/6883 | (2018.01) |
| C12Q 1/34 | (2006.01) |

(52) U.S. Cl.
CPC ............ *G01N 33/573* (2013.01); *C12N 9/80* (2013.01); *C12Q 1/34* (2013.01); *C12Q 1/6883* (2013.01); *G01N 33/6893* (2013.01); *C12Q 2600/118* (2013.01); *C12Q 2600/158* (2013.01); *G01N 2333/98* (2013.01); *G01N 2800/245* (2013.01); *G01N 2800/324* (2013.01); *G01N 2800/7019* (2013.01)

(58) Field of Classification Search
CPC .......................... C12Q 1/6883; C12Q 2600/158
See application file for complete search history.

(56) References Cited

U.S. PATENT DOCUMENTS

2007/0122806 A1* 5/2007 Strom .................. C12Q 1/6883
435/6.16

FOREIGN PATENT DOCUMENTS

| CN | 102105794 A | 6/2011 |
|---|---|---|
| EP | 2 063 271 A1 | 5/2009 |
| WO | WO 03/025571 A1 | 3/2003 |
| WO | WO 2004/074815 A2 | 9/2004 |
| WO | WO 2010/083121 A1 | 7/2010 |
| WO | WO 2011/015446 A | 2/2011 |

OTHER PUBLICATIONS

Liang C.R.Y.M. et al. Proteomics 2005, 5, 2258-2271.*
M. P. Welberry Smith et al, "A Novel Proteomic Marker for Delayed Graft Function", American Transplant Congress 2012 Abstracts, Abstract# 813; Poster Board #-Session: P281-I, American Journal of Transplantation, vol. 12, Issue Supplement s3, pp. 269, May 2012.*
Cheung V.G. et al., Nature Genetics, vol. 33, Mar. 2003, pp. 422-425.*
Chen G. et al. Molecular & Cellular Proteomics (2002), pp. 304-313.*
J. Perren Cobb et al, Crit Care Med 2002; 30:2711-2721.*
Hoshikawa, Y. et al. Physiol Genomics 12: 209-219, 2003.*
Juppner H. Bone vol. 17, No. 2, Supplement, Aug. 1995:39S-42S.*
Jin et al., iTRAQ-2DLC-ESI-MS/MS based identification of a new set of immunohistochemical biomarkers for classification of dysplastic nodules and small hepatocellular carcinoma. J Proteome Res. Aug. 5, 2011;10(8):3418-28. doi: 10.1021/pr200482t. Epub Jun. 21, 2011.
Uttamsingh et al., Immunohistochemical localization of the acylases that catalyze the deacetylation of N-acetyl-L-cysteine and haloalkene-derived mercapturates. Drug Metab Dispos. Jun. 2000;28(6):625-32.
Yamauchi et al., Tissue distribution of and species differences in deacetylation of N-acetyl-L-cysteine and immunohistochemical localization of acylase I in the primate kidney. J Pharm Pharmacol. Feb. 2002;54(2):205-12.
Zhong et al., Genome-wide analysis identifies a tumor suppressor role for aminoacylase 1 in iron-induced rat renal cell carcinoma. Carcinogenesis. Jan. 2009;30(1):158-64. doi: 10.1093/carcin/bgn255. Epub Nov. 21, 2008.
Abu Jawdeh et al., Delayed kidney allograft function—what does it tell us about acute kidney injury? Contrib Nephrol. 2011;174:173-81, doi: 10.1159/000329395. Epub Sep. 9, 2011. Review.
Klawitter et al., Association of immunosuppressant-induced protein changes in the rat kidney with changes in urine metabolite patterns: a proteo-metabonomic study. J Proteome Res. Feb. 5, 2010;9(2):865-75. doi: 10.1021/pr900761m.
Kusaka et al., Up-Regulation of Osteopontin, Chemokines, Adhesion Molecule, and Heat Shock Proteins in 1-Hour Biopsy From Cardiac Death Donor Kidneys. Transplantation Proceedings. Dec. 2006;38(10):3347-50.
Magistroni et al., Interstitial fluid obtained from kidney biopsy as new source of renal biomarkers. J Nephrol. May-Jun. 2011;24(3):329-37. doi: 10.5301/JN.2010.5707.
Miller et al., Monoclonal antibody based immunoassay for human aminoacylase-1. J Immunoassay. 1989;10(2-3):129-52.

(Continued)

*Primary Examiner* — Stephen T Kapushoc
(74) *Attorney, Agent, or Firm* — Wolf, Greenfield & Sacks, P.C.

(57) ABSTRACT

The invention relates to use of ACY-1 as a biomarker for ischaemia-reperfusion injury.

3 Claims, 13 Drawing Sheets

Specification includes a Sequence Listing.

(56) References Cited

OTHER PUBLICATIONS

Welberry Smith et al., Serum aminoacylase-1 is a novel biomarker with potential prognostic utility for long-term outcome in patients with delayed graft function following renal transplantation. Kidney Int. Dec. 2013;84(6):1214-25. doi: 10.1038/ki.2013.200. Epub Jun. 5, 2013.
Liu et al. On the Dependency of Cellular Protein Levels on mRNA Abundance. Cell. Apr. 21, 2016;165(3):535-50. doi: 10.1016/j.cell. 2016.03.014.
Smith et al. A Novel Proteomic Marker for Delayed Graft Function. University of Leeds. Poster Presentation. Presented Jun. 2012 at the American Transplant Congress, Boston, MA.
Smith et al. A Novel Proteomic Marker for Delayed Graft Function. American Transplant Congress 2012 Abstracts. Abstract # 813. Poster Board Session: P281-I. Am Journal of Transplantation. 2012. vol. 12. p. 269.

\* cited by examiner

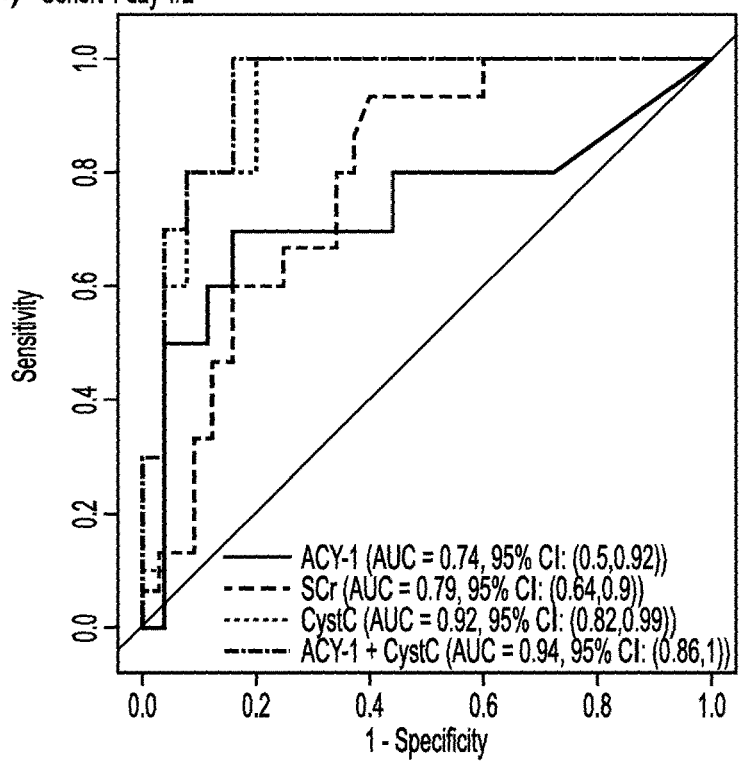
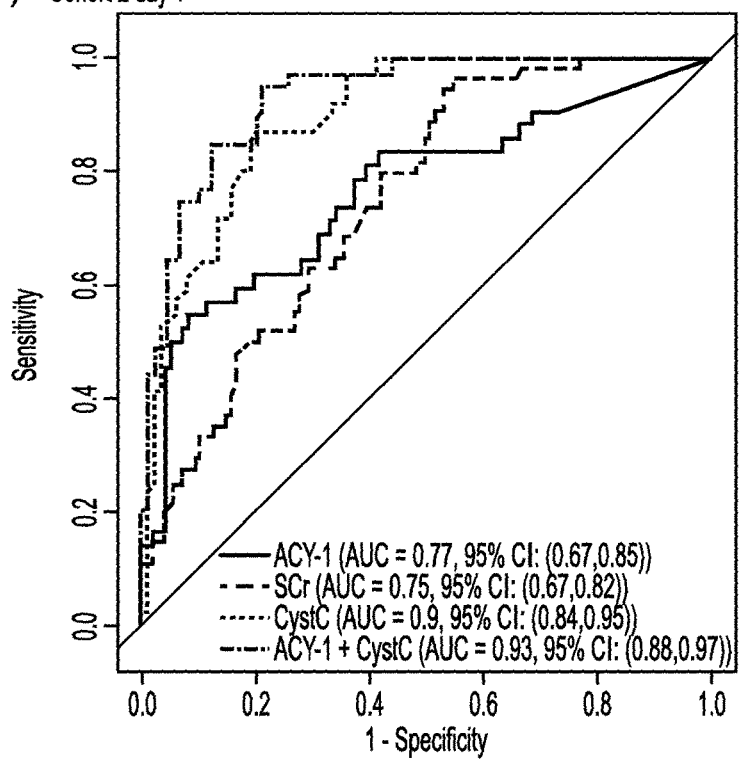
FIG. 5

SEQ ID NO:1

```
   1 ggcggcgctg gccgcggcgg ccgctgcccg gggacgggat ccggatctaa tcctccagta
  61 atctcgctga ggcccgaacc agaggcgggc ggggacatcc gcgccgacgc ggccgctggc
 121 gccgggacgg ccctcactga cggtcttcgg tctccgcccc gacatccggc ctcggccacg
 181 tggtgggcgg accggggcgg tcctgagcct gcgacctcgc aggcgacctc gctggaccct
 241 aagtccaggc cacagtcagg aagggcgct gagaggcgag cgtgagccca gcgacaggag
 301 agtgaggtgg gggccctggg gagggataga gggactgggg ctccgtggct tgaaagccgg
 361 gcaactggga ggcgttgggg tttttcttgt ttgtttttg ttttgtttt tgccttttt
 421 ttttttagg agggcggggg gagtacaagt ctgggttcaa accttgctca gctactctat
 481 gagctgtcct tgaacctctc tgagcctctc agctttctcc tctgtaaagt gggcattctg
 541 agcacaaact tcatggggct cttttgggga ttaaataagg aaatgtgctg gaagcagaca
 601 gcccagcgcc tgaaacagaa tgggtgctcc ttaatggggg ctccgaaaca cggtatccta
 661 cccctgtggg aagtccggga gccgccgtgg ggacaggctg tgtgcaggag ctcaccattt
 721 ccagggtctt ggagggtag ttagccattc actttgcccc cagctcacca cgcgcagcgc
 781 catgaccagc aagggtcccg aggaggagca cccatcggtg acgctcttcc gccagtacct
 841 gcgtatccgc actgtccagc ccaagcctga ctatggtgag aagacggtgg ttccagagcc
 901 tgtgacgggg cctaagggac ggggactgtg ctctaaacca gcctccaacc cctgtcaccc
 961 agctgagccc cactctgctg tcccaaatgg ctccccaacc cctccagcca ttccccaagt
1021 aaatagactg aggcagcccc tccaggttag ggaggaaccc tttccccaga gactctgctg
1081 ctgaccaagg ttactcctgg cagctggtta agaaaaaact tcacctcact ctccagggca
1141 ggagtggtgg gggaagcctg aggcagccac agggaaagga gaggccctcc agaagcccac
1201 tggggctgga caaaggccac agcccttagg gagtcaagct tggtggctag ggcctgggag
1261 gtggctcctg cctgttatcc cagcacttca ggaggttgag gctggcagat tgcttgggcc
1321 caggagttca agactagctt gagcaacatg gcaagactct gtctctacag aaaaaataca
1381 aaaattagtc aggaatggtg gcacacctgt agtcccagct actccagagg ttgaggtggg
1441 aggatcgctt gagcctggga ggttgaggct gcagtgagcc gagatcgcac cacttcactc
1501 ctgccttggt gacagagtga gaccctgtct caaaaaaaaa aaaaaaaaaa ggaaaagaaa
```

FIG. 6

1561 aaaaaaaaac ttagtggctg ggaattgtgt acatgggtcc aaattcctcc tctgtgatta 1621 atcagctgag agatggtggg tgaatctctt catgtctctg tgccatagtt tcccatattt 1681 aaggaagata acaccttcct ccaaccctgt gtccagacat cccctggac ttccagaaag 1741 ggtcactgag tagccaaaaa tatcttcttt cttggggatg gaaatgcaag catctctgag 1801 ggatatggag tgtgtcgggg aggcagcagc ccatttctgg gtatgctcca ctctccgggc 1861 tgcctgggct ggtgggaagc tgtgggtagg cagaagcagc cccaagacac tctgtgcctc 1921 caggagctgc tgtggctttc tttgaggaga cagcccgcca gctgggcctg ggctgtcaga 1981 aagtagaggt gagcctgggg ccctaagcgg ggaagggagg tgggcctggg cacttcctca 2041 ccctgctcag accacctacc ctcctgacca tctccaggtg gcacctggct atgtggtgac 2101 cgtgttgacc tggccaggca ccaaccctac actctcctcc atcttgctca actcccacac 2161 ggatgtggtg cctgtcttca aggtgtgtaa ggggctgggg aggtgggcag tgcaggcctt 2221 ggggacagac atgatgcaga ccccaggatt caacctcaag ttgctcatgg tcctggcccc 2281 agtcctgaca ctaactctca acatccttat gacattacac cactcaagca gccttcatcc 2341 agcagcaagt tctgggccag agtggggtgg ggactggggg gtgggaagca ggagacagca 2401 atgggggatg gcaatcagct gccttcttca gcccccgtct ttcctctccc accactccac 2461 ctgtcactcc aaccctatgg tgggctccta gggcagggcc actgttgacc agagtggatt 2521 aatggctaaa tttggggttt gggcccctct tcccatccct gcccccagga acattggagt 2581 cacgacccct ttgaggcctt caaggattct gagggctaca tctatgccag gggtgcccag 2641 gacatgaagt gcgtcagcat ccagtgagtg tcctccattc ctactcctcc acaatgtccc 2701 cactggtcca gtggattgaa gcaggacctg aggggtgat tggagaaact caaggccaag 2761 gaacaccgtg acctcttgga caggaactac tgccatgacc attgcatgga tagggagatt 2821 cagaccagag aggggcaggg acttctgga gtccctatca gggtgtggca gggtaaagtc 2881 caggacacag gactccagcc tgctggccct gcctgtgggg ccagcctgcg catctggtgg 2941 ctcccccagc acctggctta tgccccctca ggtacctgga agctgtgagg aggctgaagg 3001 tggagggcca ccggttcccc agaaccatcc acatgacctt tgtgcctggt aggagtggct 3061 cagatacctt tgggaaaggg gagggtgggg cggggcagcc tcctcatctc acgtccctgc 3121 tgcttttaca gatgaggagg ttgggggtca ccaaggcatg gagctgttcg tgcagcggcc 3181 tgagttccac gccctgaggg caggctttgc cctggatgag ggtgagcagg ttggcaagcc

FIG. 6 (continued)

3241 aatgagcagc caggcaggga gtaggaggct gctagtgggg actgagctgc tccaccctct
3301 gaaccccctt tccctcctca ggcatagcca atcccactga tgccttcact gtcttttata
3361 gtgagcggag tccctggtgt aagtatgagc ttggagggag ggctcactct acaggcggga
3421 ggctaggcca gaaagggcac ggtcctatgc agggttgcac agcaaagttg aggcctgaga
3481 aggccttgaa cccagggcct ctacctccca gctctttcct atctgagctt ctctgagggc
3541 aagccctgaa tgggcagaaa ccagctgtat gctacgggcc ctgagtgggg acaggaccct
3601 gccagaggag cctggaatga gggggagacc tgggcccacc ccaggctgat tgtgtctcca
3661 gcccctcagg ctgaagacac tgccttcccc ctacacctcc ccaggggtgc gggttaccag
3721 cactgggagg ccaggccatg cctcacgctt catggaggac acagcagcag agaagctggt
3781 acgtggcacc ccaggaggga gtctgggagt tcaggaggct ctatcctgag gccactgtcc
3841 catttaacct catattctca tagcacaagg ttgtaaactc catcctggca ttccgggaga
3901 aggaatggca gaggtgaggc agcctgggag gcagtggggt ggctctggga ggcggtacca
3961 cagaggatag agtctgagcc acctctttta tctgttgctg ccgctaccct gcccccacac
4021 cacaggctgc agtcaaaccc ccacctgaaa gaggggtccg tgacctccgt gaacctgact
4081 aagctagagg gtggcgtggc ctataacgtg atacctgcca ccatgagcgc cagctttgac
4141 ttccgtgtgg caccggatgt ggacttcaag gtgccacctc cacctgggtt tggaggaggg
4201 atcctgggtc ctcagtcttg tcctagaggc ctctggaaag cctgaaggat cagctcgtct
4261 cccttctctt aggcttttga ggagcagctg cagagctggt gccaggcagc tggcgagggg
4321 gtcaccctag agtttgctca ggtatggact tgggacatgt gatgggagag tgtgggagcc
4381 gggggagacc caagtgtgca acagtggagt gtgtgcttgg tgtgtctgca tatgtctggg
4441 catttctttta tctgtgacag acacatttta ttccaacaag cattcattgt agaggccact
4501 gtgggtgctg gggaatgctg tggggagtaa aattaggcac agttcatgcc cttgtatggt
4561 gaaacgggga gatataaatc aaacatttat gtgatattac ttttttctga gagaatctca
4621 ctccgtcacc caggctgcag tgcagtggca caatctcggc tcacctccgc ctcccgggtt
4681 caagcaattc ttgtgcctca gcctccagag tagttgggat tacaggcacc tgccaccacg
4741 cccagctaat ttttgcattt ttagtagaga cagtgtttca ccatgttggc caggcttgtc
4801 tcgaactcct ggcctcaagt gatccaccca ccttggcctc gcaaaatgct gggattacag
4861 gcatgagcca ctgcgcccag ccgtactttc atataaccca tgtggtacag gaaagggtgg

FIG. 6 (continued)

4921 ccccttgcac tctgaaaacc tgtaactgga gtatccaact agtctgagag gtctggggga 4981 gccatcttga ggaaggggca cttgggctag gatctgaagg atggacagga ggtaagtaga 5041 cggagggtgg gaaggtccca gacctaggac atttgagggg ctgaaagagg acctgtggct 5101 ggactggcta cccagatgtc tgggtaggtg aaggagtggg ggtggggagg tgttatgtac 5161 taggcacagc ccactctatg ggaaatagg caagatgccc aggcccatgt cctgatcctg 5221 ccattcttcc tgtccctcag aagtggatgc acccccaagt gacacctact gatgactcaa 5281 acccttggtg ggcagctttt agccgggtct gcaaggatat gtgagcacgc tggccagctc 5341 tcctcacagc ccagccccct actcctctcc ttcctgctgc cccctccctt ctccctcctt 5401 ctcccacctc tttcccacct tcctttgccc cttcaattct tcgctttctc cctccccatt 5461 catcaggctc tttctcctac aggaacctca ctctggagcc tgagatcatg cctgctgcca 5521 ctgacaaccg ctatatccgc gcggtgagcc acttgcatat agtgcctggg cagtggactg 5581 ggcctgagtg ctggcttttc cctaacggct cttcctcacc cctgcaggtg ggggtcccag 5641 ctctaggctt ctcacccatg aaccgcacac ctgtgctgct gcacgaccac gatgaacggc 5701 tgcatgaggc tgtgttcctc cgtggggtgg acatatatac acgcctgctg cctgcccttg 5761 ccagtgtgcc tgccctgccc agtgacagct gagccctgga actcctaaac ctttgcccct 5821 ggggcttcca tcccaaccag tgccaaggac ctcctcttcc cccttccaaa taataaagtc 5881 tatggacagg gctgtctctg aagtactaac acaaggaca

FIG. 6 (continued)

SEQ ID NO:2

```
MTSKGPEEEH PSVTLFRQYL RIRTVQPKPD YGAAVAFFEE TARQLGLGCQ KVEVAPGYVV
TVLTWPGTNP TLSSILLNSH TDVVPVFKEH WSHDPFEAFK DSEGYIYARG AQDMKCVSIQ
YLEAVRRLKV EGHRFPRTIH MTFVPDEEVG GHQGMELFVQ RPEFHALRAG FALDEGIANP
TDAFTVFYSE RSPWWVRVTS TGRPGHASRF MEDTAAEKLH KVVNSILAFR EKEWQRLQSN
PHLKEGSVTS VNLTKLEGGV AYNVIPATMS ASFDFRVAPD VDFKAFEEQL QSWCQAAGEG
VTLEFAQKWM HPQVTPTDDS NPWWAAFSRV CKDMNLTLEP EIMPAATDNR YIRAVGVPAL
GFSPMNRTPV LLHDHDERLH EAVFLRGVDI YTRLLPALAS VPALPSDS
```

FIG. 7

USE OF ACY-1 AS A MARKER OF ISCHAEMIA/REPERFUSION, DELAYED GRAFT FUNCTION AND GRAFT VIABILITY AS WELL AS METHOD THEREOF

This invention relates to a biomarker for ischemia-reperfusion injury or delayed graft function. Specifically the invention relates to aminoacylase-1 and methods of diagnosis and prognosis using the aminoacylase-1.

BACKGROUND

Renal transplantation provides clear benefits for patients with end stage kidney disease[1,2], and significant cost savings compared to dialysis[3,4]. In 2010, 16,151 renal transplants were performed in the USA (http://optn.transplant.hrsa.gov), with the corresponding figure for the UK being 2,687 (http://www.uktransplant.org.uk). However, a proportion of patients experience early complications which can significantly impact the clinical and health economic outcomes, such as delayed graft function (DGF)[5].

A number of definitions of DGF have been proposed[6-8] with one commonly used being the need for dialysis in the first week after renal transplantation, other than for isolated hyperkalaemia. Although there are parallels with acute kidney injury seen in other clinical situations, the pathology underlying DGF is complex with contributions from donor-derived factors such as donor age and duration of ischaemia, and recipient factors such as reperfusion injury, immunological responses and immunosuppressant medications[9]. Acute tubular necrosis (ATN) secondary to ischaemia-reperfusion injury (IRI) is the predominant histological finding in patients with DGF, but acute cellular or humoral rejection may occur concurrently, and other pathologies are sometimes apparent histologically, e.g. calcineurin inhibitor toxicity. Increasing use of organs donated after circulatory death (DCD) and from extended criteria donors[10], has corresponded with an increase in the incidence of DGF which currently affects ~20% of transplant recipients in the USA[5]. DGF increases the risk of graft failure, patient death and death-censored graft failure by 2-3 fold[11,12], and is associated with a number of complications that contribute to reduced longer-term graft survival, such as a poor transplant function at one year, arterial hypertension, and acute rejection[13]. Overall, DGF has been associated with a 41% increased risk of graft loss at just over 3 years[14].

Early identification of DGF and increased understanding of the specific underlying pathology has significant potential to improve immediate patient management[15], allowing fluid volume status optimisation, timely appropriate dialysis, and avoidance of unnecessary investigation and treatment. The opportunity to stratify patients and tailor specific therapeutic interventions at an earlier time point may in turn result in improved longer-term outcomes. With developments in proteomic technologies, there is increasing excitement about the potential of clinical proteomics in identifying new biomarkers with clinical impact[16], complementing promising markers emerging from genomic-based studies.

Urinary markers currently under investigation as potential predictors of requirement for dialysis and graft recovery after transplantation include interleukin 18 (IL-18) and neutrophil gelatinase lipocalin (NGAL)[17], with tissue-associated markers including ICAM-1 and VCAM[15,18]. Unfortunately, in the majority of cases of DGF, urine is not produced or may be mixed with residual native renal output confounding analysis of any results and biopsied tissue is often only available relatively late once DGF is established. Although NGAL and IL-18 have not shown promise when analysed in serum[19], blood-borne biomarkers would be an ideal way of monitoring post-transplantation due to the accessibility and routine use in hospital laboratories. However, biomarker discovery with serum or plasma is challenging with only 22 proteins comprising ~99% of the total protein mass, and the wide dynamic range of protein abundances spanning ~10 orders of magnitude[20].

As discussed above, a number of potential biomarkers have been associated with renal ischaemia-reperfusion injury, such as NGAL, IL-18, KIM-1, L-FABP, netrin-1, and keratinocyte-derived chemokine, though the majority of these have been studied in urine, and in native acute kidney injury (AKI) rather than post-transplantation in the context of DGF. Urinary NGAL and IL-18 have been examined in DGF with AUCs of 0.78 and 0.77 at 18 h post transplant. Encouraging though these results appear, they are subject to the difficulties of whether urine output occurs at all post-transplant in DGF and where such output is confounded by ongoing urine productive from native kidneys. Furthermore, whilst urinary NGAL has been proposed as a marker to distinguish pre-renal from intrinsic renal failure in AKI, and similar use in transplant patients might be imagined, its true ability to discriminate is questionable. NGAL and IL-18 have been studied in serum in DGF and SGF, but no discrimination between groups was seen, whereas Cystatin C did discriminate, outperforming serum creatinine. Donor urinary NGAL, but not serum NGAL has been associated with prolonged DGF. Despite the numerous candidates for biomarkers in IRI, and the investigations to date of promising markers like NGAL and IL-18, as yet no candidate marker in serum has emerged with clear clinical utility.

Delayed graft function remains a major clinical concern in renal transplantation, not only because of the impact on length of patient stay and associated costs, but because of the difficulty in managing patient's fluid status, and the timely, appropriate use of dialysis (especially haemodialysis) to avoid possible further clinical complications which can occur with over-zealous fluid removal from "wet" post-transplant patients who are exhibiting minimal renal function. Furthermore, the known negative longer term impact on patients who experience DGF means this is of significant importance to practicing renal transplant clinicians.

Accordingly, there remains a need for a blood-borne biomarker predictive for ischaemia-reperfusion injury, such as DGF.

BRIEF SUMMARY OF THE DISCLOSURE

In accordance with the present inventions there is provided use of ACY-1 as a biomarker for ischaemia-reperfusion injury. Preferably, said ischaemia-reperfusion injury is in at least one tissue selected from brain, heart, kidney, lung and liver.

Preferably said ischaemia-reperfusion injury is caused by myocardial infarction, stroke, surgery, injury or organ transplantation.

Preferably said ischaemia-reperfusion injury results in delayed graft function in a post operative organ transplant patient. Preferably, said post operative organ transplant patient is a post operative renal transplant patient.

In a further aspect the invention provides use of ACY-1 as a biomarker for delayed graft function.

In a further aspect the invention provides a method of diagnosing an ischaemia-reperfusion injury in a patient comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level identifies the patient as having an ischaemia-reperfusion injury.

Preferably, said ischaemia-reperfusion injury is in at least one tissue selected from brain, heart, kidney, lung and liver. Preferably said ischaemia-reperfusion injury is caused by myocardial infarction, stroke or organ transplantation.

Preferably said patient is a post operative renal transplant patient.

In a further aspect the invention provides a method of diagnosing delayed graft function in a transplant patient comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level identifies the patient as having delayed graft function.

Preferably said patient is a post operative renal transplant patient.

In a further aspect the invention provides a method of determining a dialysis management strategy for a post operative renal transplant patient comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level identifies that the patient will require dialysis within 1 to 7 days post transplantation or wherein a decreased level of ACY-1 in the patient sample compared to the control sample or compared to the predetermined reference level identifies that the patient will not require dialysis within 1 to 7 days post transplantation.

In a further aspect the invention provides a method of determining a fluid management strategy for a post operative renal transplant patient, comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level identifies that the patient requires a reduced amount of fluid compared to that normally administered to a post-operative renal transplant patient, or wherein a decreased level of ACY-1 in the patient sample compared to the control sample or compared to the predetermined reference level identifies that the patient will benefit from an increased amount of fluid compared to that normally administered to a post-operative renal transplant patient, since dialysis is less likely to be required.

In a further aspect the invention provides a method of predicting a post operative clinical outcome of a renal transplant in a patient, comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level is prognostic of an increased death free and/or dialysis free survival rate for said patient at 1, 2, 3, 4 or 5 years post transplantation.

Preferably the sample is a blood sample, more preferably a serum sample.

Preferably said sample is obtained from said patient post transplantation.

Preferably said sample is obtained from said patient 1, 2, 3 or 4 days post transplantation. Preferably said patient is human.

Preferably said ACY-1 is a human ACY-1. Preferably said ACY-1 is a polypeptide. Preferably said polypeptide has the amino acid sequence of SEQ ID NO:2. Alternatively said ACY-1 is a nucleic acid molecule, such as an mRNA. Preferably said nucleic acid molecule has the nucleotide sequence of SEQ ID NO:1.

Preferably said predetermined reference level is the average level of ACY-1 in a control patient.

Preferably the methods of the invention further comprise: i) determining the level of at least one biomarker select from NGAL, KIM-1, IL-18, RBP, FABP4, cystatin C and creatinine in a sample isolated from the patient; and ii) comparing the level of NGAL, KIM-1, IL-18, RBP, FABP4, cystatin C or creatinine in the patient sample with the level of NGAL, KIM-1, IL-18, RBP, FABP4, cystatin C or creatinine in a control sample or with a predetermined reference level for NGAL, KIM-1, IL-18, RBP, FABP4, cystatin C or creatinine.

In a further aspect the invention provides a kit for diagnosing ischaemia-reperfusion injury in a patient comprising: i) a detectably labelled agent that specifically binds to an ACY-1 polypeptide or a detectably labelled agent that specifically binds to an ACY-1 nucleic acid; and ii) reagents for performing a diagnostic assay.

In a further aspect the invention provides a kit for diagnosing delayed graft function in a patient comprising: i) a detectably labelled agent that specifically binds to an ACY-1 polypeptide or a detectably labelled agent that specifically binds to an ACY-1 nucleic acid; and ii) reagents for performing a diagnostic assay.

In a further aspect, the invention provides an assay device comprising a compound or agent capable of detecting an ACY-1 polypeptide.

In a further aspect, the invention provides a kit for diagnosing ischaemia-reperfusion injury or diagnosing delayed graft function or diagnosing kidney injury, disease or disorders in a patient comprising an assay device comprising a first antibody which specifically binds to an ACY-1 polypeptide; and (2) a second, different antibody which binds to either the ACY-1 polypeptide or the first anti-ACY-1 antibody and which is conjugated to a detectable agent.

BRIEF DESCRIPTION OF THE DRAWINGS

Embodiments of the invention are further described hereinafter with reference to the accompanying drawings, in which:

FIG. 5. ROC curves for the prediction of delayed graft function (DGF), each showing serum ACY-1, creatinine (SCr), cystatin C (CystC), and ACY-1 combined with cystatin C. a). Cohort 1 results—days 1/2 post-transplant (n=47 but n=35 for ACY-1 and cystatin C); b). Cohort 2 results—day 1 post-transplant (n=194 but n=138 for ACY-1 and 128 for cystatin C).

FIG. 6. Shows the nucleotide sequence of human ACY-1, SEQ ID NO:1.

FIG. 7. Shows the amino acid sequence of human ACY-1, SEQ ID NO:2.

DETAILED DESCRIPTION

Figure 1:
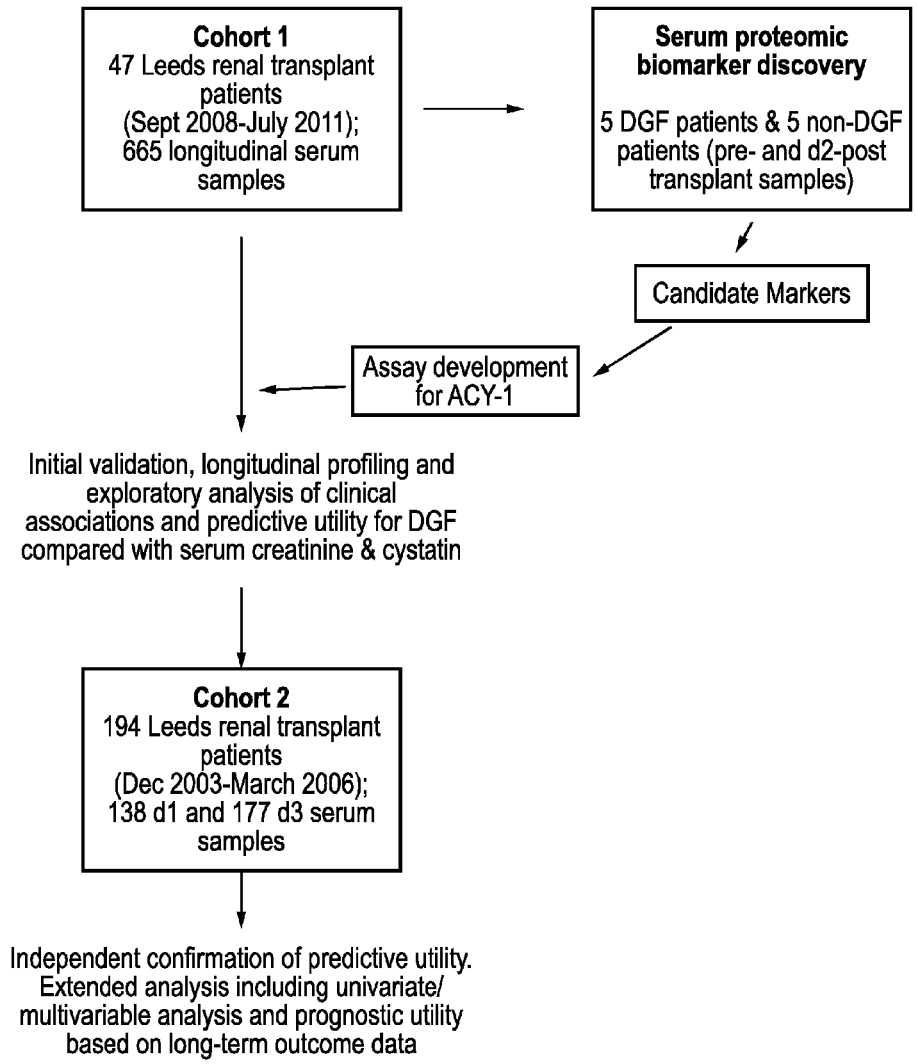
FIG. 1. Shows patient groups and study design

The inventors compared serum proteins pre- and post-operatively from patients undergoing renal transplantation, with and without DGF, employing immunodepletion of 14 of the most abundant proteins coupled with high mass accuracy LTQ-Orbitrap Velos label-free analysis, previously shown to produce a moderate depth of proteomic coverage with good reproducibility[21]. The inventors surprisingly identified a key candidate as aminoacylase-1 (ACY-1). Following assay development allowing the measurement of ACY-1 in serum for the first time, validation in larger cohorts of patients confirmed the potential clinical utility of ACY-1 as a marker for IRI and DGF in samples as early as day 1 post-transplant and importantly a significant association with outcome was seen.

Moreover, the identification of a serum based biomarker and the use of serum has clear advantages in the context of IRI, and in particular DGF. Patients with DGF often have no urine output at all, which impacts dramatically on the usefulness of urinary markers. Residual native urine output further complicates the assessment and use of urinary markers in this clinical situation.

ACY-1 was identified as a biomarker for DGF from the proteomic analysis of serum. The biomarker provides for early delineation of patient groups after renal-transplantation in a clinically useful manner, and demonstrates the possibility of taking clearly defined clinical questions, with carefully collected and annotated clinical sample sets, through a robustly developed proteomic method, candidate selection and clinical test development system, to the brink of clinical utility.

The inventors have been able to derive a marker of potential clinical utility from proteomic analysis of serum, through the development of both 1) the necessary methodology in coupling reproducible immunodepletion with high mass accuracy tandem mass spectrometry using an Orbitrap Velos mass spectrometer[21]; and 2) the use of an integrated team of clinicians and scientists spanning the discovery and initial validation stages of the biomarker pipeline and a high quality bank of samples prospectively collected with associated clinical data.

Aminoacylase-1 (ACY-1)

Aminoacylase-1 (ACY-1), also called N-acyl-L-amino-acid amidohydrolase) belongs to the peptidase M20A family, and is thought to be involved in hydrolysis of N-acylated or N-acetylated amino acids (except L-aspartate), producing a carboxylate and an L-amino acid. ACY-1 is a zinc-binding homodimeric cytoplasmic protein with a predicted monomeric mass of 45.8 kDa[22]. In eukaryotic cells, 50-80% of all cellular proteins are acylated at the N terminus, a co- or post-translational modification which can affect protein function and stability. ACY-1 catalyses the hydrolysis of N-acylated peptides, particularly the N-acetylated neutral aliphatic amino acids, releasing free amino acids for protein synthesis[23]. The highest levels of expression and activity are found in the kidney followed by liver, brain, skeletal muscle and pancreas and low expression in several other organs[22,24-27]. Pan-tubule ACY-1 expression has been shown in the pig kidney[26] with predominantly proximal tubule expression in human kidney[26] with a proposed role in amino acid salvage[28]. An inborn error of metabolism with variable neurological features has been associated with ACY-1 mutations, with effects on ACY-1 expression and activity depending on the mutation[29] and increased urinary N-acetylated amino acids[25]. Located on chromosome 3p21.1, a role as a tumour suppressor gene has been proposed in both renal and lung cancers[22,30,31].

The low or undetectable serum ACY-1 concentrations pre-transplantation and the absence of any increase with infection, or post-surgery in live donors, suggests the post-transplant elevation of ACY-1 in DGF is not simply due to impaired renal clearance or a consequence of inflammation. DGF is complex with multiple risk factors and underlying mechanisms involving various cells including tubules and the vasculature, from preprocurement through to the post-operative period.[9,32] Assuming a renal tubular source, the increased serum ACY-1 in many cases of DGF could reflect the extent of tubular damage and this is supported by the association with ATN (although the number of biopsies was small) and the trend in serum ACY-1 concentrations from uncomplicated transplants through slow graft function to DGF. Conversely the relationship between higher ACY-1 and better outcome following DGF may indicate increased synthesis and a role in the repair process, potentially via effects on amino acid availability for protein synthesis.

ACY-1 was one of 75 urinary proteins changing significantly in rats treated with cyclosporine or sirolimus (but not tacrolimus)-treated rats[33] and ACY-1 forms adducts with the biologically active metabolite generated in the kidney from mycophenolate mofetil (MMF)[34], proposed to be involved in organ toxicity. However, we found no links with CNI toxicity or MMF. Interestingly analysis of serum samples from 22 patients with AKI, 10 of whom were within 3 days of diagnosis, showed serum ACY-1 concentrations all <60 ng/mL (data not shown), possibly indicating that whether reflecting damage or repair or any possible underlying IRI, it is very specific to a pathological process encountered primarily in certain transplant situations and/or only occurs under the more extreme and extensive ischaemic/hypoxic conditions at that time. This is also supported by the marked differences in serum ACY-1 between the DBD, DCD and LD transplants.

In terms of markers for DGF, combining gene expression, particularly in chemokines CCL19 and 21 and proteasome subunits PSMB8 and 10, in zero hour biopsies from deceased and live donor grafts, with relevant clinical factors has resulted in AUC values of 0.74 for DGF and 0.93 for acute rejection[35]. Expression of RANTES and CCR1/CCR2 in biopsies from patients with DGF has also been reported to be associated with graft function at 1 year post-transplantation and later[36]. Several existing markers of use in AKI have also been examined[37,38] but tissue KIM-1 for example doesn't correlate with DGF[39] whilst urinary NGAL and IL-18 have some predictive value for DGF[17,40] but no correlation with long-term function[41]. Day 1 serum NGAL concentrations had no predictive value for DGF but similar to our study, serum cystatin C had an AUC of 0.83[17]. Our specificity (88.5%) and negative predictive values (81.7%) for ACY-1 in relation to DGF are high enough to potentially contribute to biomarker panels. Clearly serum cystatin C, which directly reflects renal function, is superior to ACY-1 in predicting DGF early with AUC similar to the 0.96 seen in a meta-analysis of its use in predicting AKI in various clinical settings[42]. However using both ACY-1 and cystatin C is slightly better on day 1 with ACY-1 having higher specificity and if a more sensitive ACY-1 assay was developed, further discrimination by ACY-1 may be possible.

Further mechanistic insight may be apparent from gene expression studies in mouse models of IRI[43]. Sphingosine kinase-1 (SphK1) catalyses the formation of sphingosine-1-phosphate which has been implicated in protection/repair in renal IRI[44-46] differs between grafts classified by function[47] and is reported to interact with ACY-1[30,48]. Inflammatory and immune-response genes in donor biopsies have been predominantly associated with IRI and DGF, with integrated systems biology analysis approaches being proposed to provide further insight[15]. A recent comparison of DGF and non-DGF pre-implantation biopsies found no significant clustering of pathways until the DGF group was subclassified on the basis of renal function during the first year, when genes implicated in T cell activation, antigen presentation and cell adhesion were associated with subsequent poorer function[47]. This subclassification of DGF patients is analogous to the situation with ACY-1 in the present study where clear elevations in serum ACY-1 post-transplant are seen in only about two-thirds of patient with DGF. This may imply different underlying pathophysiological subgroups and also demonstrates the prognostic value of ACY-1 within the DGF patient group.

Since tubular cell apoptosis and regrowth are fundamental parts of the ischaemia-reperfusion injury (IRI) experienced by the renal graft in kidney transplantation, and given the tubular localisation of ACY-1 as noted above, the possibility of ACY-1 relating to processes that might follow significant IRI, such as delayed graft function (DGF), is biologically plausible. Whilst the effects of calcineurin inhibitors and sirolimus on ACY-1 have been noted in a single study on Wistar rats, firm understanding of the biology of ACY-1 in the context of renal transplantation is lacking.

As used herein, the term "ACY-1" is used to refer to both Aminoacylase-1 polypeptides and nucleic acid molecules.

Preferably the ACY-1 is a human ACY-1 polypeptide or nucleic acid molecule.

As used herein, the term "nucleic acid molecule" includes DNA molecules (e.g., a cDNA or genomic DNA) and RNA molecules (e.g., a mRNA) and analogs of the DNA or RNA generated, e.g., by the use of nucleotide analogs. The nucleic acid molecule can be single-stranded or double-stranded, but preferably is double-stranded DNA.

In one embodiment the ACY-1 nucleic acid molecule comprises the nucleotide sequence shown in SEQ ID NO:1, or a fragment of any of this nucleotide sequence. In one embodiment, the nucleic acid molecule consists of the nucleotide sequence of SEQ ID NO:1, or a fragment of any of this nucleotide sequence.

In another embodiment, an isolated the ACY-1 nucleic acid molecule is a nucleic acid molecule which is a complement of the nucleotide sequence shown in SEQ ID NO:1, or a fragment of any of this nucleotide sequence. In other embodiments, the nucleic acid molecule of the invention is sufficiently complementary to the nucleotide sequence shown in SEQ ID NO:1 such that it can hybridize to the nucleotide sequence shown in SEQ ID NO:1 under hybridization conditions, thereby forming a stable duplex. Preferably, the hybridization conditions a high stringency hybridization conditions.

As used herein, the phrase "high stringency hybridization conditions" describes conditions for hybridization and washing. Stringent conditions are known to those skilled in the art and can be found in available references (e.g., Current Protocols in Molecular Biology, John Wiley & Sons, N.Y., 1989, 6.3.1-6.3.6). Aqueous and non-aqueous methods are described in that reference and either can be used. A preferred example of stringent hybridization conditions are hybridization in 6× sodium chloride/sodium citrate (SSC) at about 45° C., followed by one or more washes in 0.2×SSC, 0.1% (w/v) SDS at 50° C. Another example of stringent hybridization conditions are hybridization in 6×SSC at about 45° C., followed by one or more washes in 0.2×SSC, 0.1% (w/v) SDS at 55° C. A further example of stringent hybridization conditions are hybridization in 6×SSC at about 45° C., followed by one or more washes in 0.2×SSC, 0.1% (w/v) SDS at 60° C. Preferably, stringent hybridization conditions are hybridization in 6×SSC at about 45° C., followed by one or more washes in 0.2×SSC, 0.1% (w/v) SDS at 65° C.

Particularly preferred stringency conditions (and the conditions that should be used if the practitioner is uncertain about what conditions should be applied to determine if a molecule is within a hybridization limitation of the invention) are 0.5 molar sodium phosphate, 7% (w/v) SDS at 65° C., followed by one or more washes at 0.2×SSC, 1% (w/v) SDS at 65° C.

In one embodiment, the ACY-1 nucleic acid molecule of the present invention comprises or consists of a nucleotide sequence which is at least about: 60%, 65%, 70%, 75%, 80%, 85%, 90%, 91%, 92%, 93%, 94%, 95%, 96%, 97%, 98%, 99%, or more identical to the entire length of the nucleotide sequence shown in SEQ ID NO:1.

As used herein, the terms "homology" and "identity" are used interchangeably. Calculations of sequence homology or identity between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

Alternatively, the percent identity between two amino acid or nucleotide sequences can be determined using the algorithm of Meyers et al. (1989) CAB/OS 4:11-17) which has been incorporated into the ALIGN program (version 2.0), using a PAM120 weight residue table, a gap length penalty of 12 and a gap penalty of 4.

In one embodiment, a nucleic acid fragment comprises or consists of a sequence corresponding to a domain, region, or functional site of ACY-1. Alternatively a nucleic acid fragment of ACY-1 encodes an epitope bearing region of an ACY-1 polypeptide.

In preferred embodiments, a nucleic acid fragment comprises or consists of 300, 400, 500, 600, 700, 800, 900, 1000, 1100, 1200, 1300, 1400, 1500, 1600 or more consecutive nucleotides of SEQ ID NO:1.

In one embodiment the ACY-1 nucleic acid molecule comprises or consists of a nucleic acid sequence that encodes an ACY-1 polypeptide, preferably an ACY-1 polypeptide comprising or consisting of the amino acid sequence of SEQ ID NO:2, preferably a functional allelic variant. Alternatively, the ACY-1 nucleic acid molecule comprises or consists of a nucleic acid sequence that encodes an allelic variant of an ACY-1 polypeptide, preferably a functional allelic variant.

As used herein the phrase "allelic variant of an ACY-1 polypeptide", include both functional and non-functional proteins. Functional allelic variants are naturally occurring amino acid sequence variants of the ACY-1 polypeptide within a population that maintain ACY-1 activity. Functional allelic variants will typically contain only conservative substitution of one or more amino acids of SEQ ID NO:2, or substitution, deletion or insertion of non-critical residues in non-critical regions of the polypeptide.

A "non-critical" amino acid residue is a residue that can be altered from the wild-type sequence of ACY-1 (e.g., the sequence of SEQ ID NO:2) without abolishing or substantially altering ACY-1 biological activity, whereas an "essential" amino acid residue results in such a change.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In one embodiment, the ACY-1 polypeptide molecule comprises the amino acid sequence shown in SEQ ID NO:2, or a fragment of any of this amino acid sequence. In one embodiment, the polypeptide molecule consists of the amino acid sequence of SEQ ID NO:2, or a fragment of any of this amino acid sequence.

In one embodiment, the ACY-1 polypeptide comprises or consists of an amino acid sequence at least about 60%, 65%, 70%, 75%, 80%, 85%, 90%, 95%, 98% or more identical to SEQ ID NO:2. Preferably, such a polypeptide retains ACY-1 biological activity.

In one embodiment the ACY-1 polypeptide is an allelic variant of the polypeptide of SEQ ID NO:2, or a fragment of any of this amino acid sequence.

In one embodiment the polypeptide fragment encodes an epitope bearing region of an ACY-1 polypeptide, e.g. a polypeptide of SEQ ID NO:2.

In one embodiment, the ACY-1 fragment comprises or consists of a biologically active fragment of the polypeptide of SEQ ID NO:2.

As used herein, a "biologically active fragment" of an ACY-1 polypeptide includes peptides comprising amino acid sequences sufficiently homologous to or derived from the amino acid sequence of an ACY-1 polypeptide, e.g., the amino acid sequence shown in SEQ ID NO:2, which include fewer amino acids than the full length ACY-1 polypeptide, and exhibit at least one activity of an ACY-1 polypeptide. A biologically active fragment of an ACY-1 polypeptide can be a polypeptide which comprises or consists of, 10, 25, 50, 100, 200 or more consecutive amino acids of SEQ ID NO:2.

Preferably, the ACY-1 polypeptide is an allelic variant of the polypeptide of SEQ ID NO:2.

As used herein the term "ACY-1 activity" and "ACY-1 biological activity" refers to an activity of the ACY-1 polypeptide. Such activities include the ability to catalyze the hydrolysis of acylated L-amino acids to L-amino acids and an acyl group. Other activities include the ability to bind zinc.

Diagnostic and Prognostic Assays

The inventors have identified that ACY-1 was low or undetectable pre-transplantation in all patients, and concentrations in live donors remained undetectable or very low consistently. Furthermore, ACY-1 concentrations did not alter in parallel with CRP changes. These findings suggest both that ACY-1 is not functioning simply as a measure of renal function (i.e. it is not raised in end stage kidney disease patients pre-transplant) nor is it acting as an inflammatory or post-surgical marker. Rather it appears to peak, in the main, in the context of ischaemia reperfusion injury or other damage/repair processes of sufficient degree to influence the speed with which the transplant functions post-operatively—being elevated significantly compared to uncomplicated transplants in both SGF and DGF. In keeping with ACY-1 being located in the renal tubules, when, in a single patient, sufficient tacrolimus toxicity occur (which in itself causes tubular damage), the inventors observed a relatively small increase in ACY-1 in parallel. However, ACY-1 was not affected by the smaller, more usual fluctuations in tacrolimus levels seen clinically, nor by positive mid-stream urine cultures (even when these were associated with clinically significant pathophysiology evidenced by high CRP concentrations and the need for inpatient intravenous antibiotic therapy).

ACY-1 serum concentrations on day 1 were significantly associated with DGF and just failed to reach statistical significance in multivariate analysis. The possibility of a marker informing clinical management as early as day 1 post-transplantation is clearly particularly advantageous. It is of note that the specificity and negative predictive values for ACY-1 in relation to DGF are high enough to be of clinical utility—meaning a low ACY-1 concentration might more reliably define the group of patients who will not go on to require dialysis; whereas sensitivity and positive predictive value, whilst reasonable in cohort 1, were not high in cohort 2. Nonetheless, the AUCs seen on ROC analysis are also high enough for clinical utility, at 0.74 and 0.77 in cohorts 1 and 2 respectively. Notwithstanding the difficulties of comparing a potential novel biomarker to an imperfect gold standard such as serum creatinine, ACY-1's utility in the current clinical environment post-transplantation can be seen from the AUCs in combination with cystatin C (0.94 and 0.93 in cohorts 1 and 2).

The inventors did not observe correlations between ACY-1 concentrations and either length of DGF (defined by days to plateau of serum creatinine) or longer term renal function parameters (creatinine, eGFR, uPCR) at one, three or five years. However, the inventors surprisingly identified that amongst those patients with DGF, those with higher ACY-1 concentrations have greater dialysis-free survival at 5 years, as a group, by Kaplan Meir analysis. This suggests that high ACY-1 concentration during the IRI post-transplantation is actually protective, even necessary, for a graft to ameliorate the IRI to sufficient degree that the graft suffers no longer term disadvantage, and this might prove a fertile area for further investigation.

Accordingly, the inventors have identified ACY-1 as a biomarker of particular use in predictive medicine (e.g., diagnostic assays and prognostic assays).

The data provided by the inventors identifies ACY-1 as being of use as a biomarker for ischemia-reperfusion injury, where the level of ACY-1 can identify patients having, or at risk of developing, ischemia-reperfusion injury.

As used herein "ischemia-reperfusion injury" refers to tissue damage caused when a blood supply returns to a tissue after a period of ischemia or lack of oxygen. The absence of oxygen and nutrients from blood during the ischemic period creates a condition in which the restoration of circulation results in inflammation and oxidative damage through the induction of oxidative stress. Any tissue may be subject to ischemia-reperfusion injury. Particularly susceptible tissues include brain, heart, kidney, lung, liver and skeletal muscle.

Ischemia, and hence ischemia-reperfusion injury may occur in myocardial infarction, sepsis, stroke and organ and tissue procurement and transplantation. Organs which may be subject to ischemia and subsequent ischemia-reperfusion injury upon transplantation include the heart, kidneys, liver, lungs, pancreas, intestine, and thymus.

Ischemia-reperfusion injury has been known to result in delayed graft function in post operative transplant patients. As used herein "delayed graft function" refers to failure/delay of the renal transplant to function adequately post-operatively, as determined by any clinical definition, including, but not limited to: the need for dialysis (for any reason) after transplantation or failure of serum creatinine (or any other marker of renal function, including calculated parameters such as creatinine clearance) to improve as anticipated. For example, delayed graft function may be determined by a) the requirement for dialysis in the first week after renal transplantation; b) the requirement for dialysis in the first week after renal transplantation other than for isolated hyperkalaemia; c) the observance of post-operative serum creatinine levels which either increase, remain unchanged, or decrease less than 10% per day in three consecutive days in the first week after transplantation; and d) a Cockcroft calculated creatinine clearance (cCCr)<10 ml/min (DGF is then said to end when this >10 ml/min).

The data provided herein identifies ACY-1 as being of use as a biomarker for delayed graft function, where the level of ACY-1 can identify patients having, or at risk of developing, delayed graft function.

The diagnostic methods described herein can identify subjects having, or at risk of developing, ischemia reperfusion injury or delayed graft function.

In one aspect the invention provides a method of diagnosing an ischaemia-reperfusion injury in a patient comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level identifies the patient as having an ischaemia-reperfusion injury.

In a further aspect the invention provides a method of diagnosing delayed graft function in a transplant patient comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level identifies the patient as having delayed graft function. The invention also provides a method of diagnosing delayed graft function in a transplant patient comprising: i) determining the level of ACY-1 in a sample isolated from a renal transplant tissue prior to transplantation or in a sample of perfusate fluid after perfusion of a renal transplant tissue; and ii) comparing the level of ACY-1 in the sample isolated from a renal transplant tissue with the level of ACY-1 in a control sample or with a predetermined reference level for ACY-1, wherein an increased level of ACY-1 in the patient sample compared to the control sample or compared to the predetermined reference level identifies the patient as having delayed graft function.

As described in the examples the inventors have identified that the level of ACY-1 in patients having an ischaemia-reperfusion injury, and in particular in patients having delayed graft function, is increased in comparison to patients not having an ischaemia-reperfusion injury. More particularly, the inventors have identified that increased levels of ACY-1, diagnostic of delayed graft function, can be identified in post-operative renal transplant patients, on days 1, 2, 3 and 4 post transplantation.

The prognostic assays described herein can be used to determine a suitable fluid management strategy, such as a dialysis management strategy, for a post-operative renal transplant patient, based upon the level of ACY-1 in a patient sample.

In one aspect the invention provides a method of determining a fluid management strategy for a post-operative renal transplant patient, comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level identifies that the patient requires a reduced amount of fluid compared to that normally administered to a post-operative renal transplant patient, or wherein a decreased level of ACY-1 in the patient sample compared to the control sample or compared to the predetermined reference level identifies that the patient will benefit from an increased amount of fluid compared to that normally administered to a post-operative renal transplant patient, since dialysis is less likely to be required.

As used herein, "fluid management strategy for a post-operative renal transplant patient" refers to the administration or withholding of either or both of oral or intravenous fluids to a patient, as determined by their clinical state/needs. For example, in DGF patients urine output is reduced, often to zero. Administering a large amount of fluid to such a patient (who has no means of excreting it) will result (ultimately) in fluid overload, manifested as oedema, including respiratory compromise from pulmonary oedema. Hence, in DGF, reduced fluid administration (compared to that required for a patient with a functioning graft) is preferable. Moreover, dialysis patients often pass little or no urine. Post-transplant, if they do not have DGF, such patients will pass a lot of urine. In such circumstances it is necessary to administer at least as much (often more) fluid to said patients. Failure to administer sufficient fluid in this context, results in the patient becoming dehydrated and which may impact upon transplant function.

There is no standard way of determining how much fluid to give someone post-transplant. It is done individually by looking at the patients urine output, and clinical state (e.g. are there signs of pulmonary oedema examining them, etc). However, in a transplant that is functioning well, significant volume of fluid is required to be administered. In a transplant with DGF, administering similar volumes of fluid is likely to be harmful.

In a further aspect the invention provides a method of determining a dialysis management strategy for a post-operative renal transplant patient comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level identifies that the patient will require dialysis within 1 to 7 days post-transplantation or wherein a decreased level of ACY-1 in the patient sample compared to the control sample or compared to the predetermined reference level identifies that the patient will not require dialysis within 1 to 7 days post-transplantation.

As used herein, "dialysis management strategy for a post-operative renal transplant patient" refers to the decision whether a post-operative renal transplant patient requires dialysis. Such strategy is revised and evaluated day by day post-operatively in renal transplant patients, and is based on fluid status and biochemical parameters like hyperkalaemia, serum creatinine and serum urea, as well as other aspects of the patients' clinical state. Sometimes dialysis decisions have to be taken urgently e.g. a patient who has DGF has been given too much fluid and now has respiratory compromise from pulmonary oedema-urgent dialysis is likely to be necessary.

The invention also provides a method of predicting a post-operative clinical outcome of a renal transplant in a patient, comprising: i) determining the level of ACY-1 in a sample isolated from the patient; and ii) comparing the level of ACY-1 in the patient sample with the level of ACY-1 in a control sample or with a predetermined reference level for ACY-1, wherein an increased level of ACY-1 in the patient sample compared to the control sample or compared to the predetermined reference level is prognostic of an increased death free and/or dialysis-free survival rate for said patient.

As used herein "post-operative clinical outcome of a renal transplant" refers to the likelihood of the transplant patient surviving or remaining dialysis-free following transplantation. The outcome may be assessed as a measure of serum creatinine levels, eGFR levels, the level of proteinuria, the presence of hypertension, survival or dialysis-free survival can all be used as measures of outcome. The post-operative clinical outcome may be the outcome at 3, 6, 12 months or 1, 2, 3, 4 or 5 years post transplantation.

The presence, level or absence of an ACY-1 polypeptide or nucleic acid molecule in a biological sample can be determined by obtaining a biological sample from a patient and contacting the biological sample with a compound or an agent capable of detecting an ACY-1 polypeptide or nucleic acid molecule.

As used herein, the term "biological sample" and "sample isolated from a patient" are used interchangeably to refer to tissues, cells and biological fluids isolated from a patient, as well as tissues, cells and fluids present within a patient. The sample may be a urine sample, a blood sample, a serum sample, a sputum sample, a faecal sample, a biopsy of body tissues, for example a biopsy of transplanted kidney tissue, a cerebro-spinal fluid sample, a semen sample or a smear sample. A preferred sample is serum or plasma. Alternatively, the sample is a perfusate fluid. In one embodiment the sample is taken pre-transplantation or alternatively post-transplantation.

As used herein "patient" refers to an individual, e.g., a human, having or at risk for having an ischemia-reperfusion injury, such as delayed graft function. In one embodiment, the patient is an individual having suffered or thought to have suffered myocardial infarction, stroke or alternatively having undergone an organ transplantation. In one embodiment, the patient is a post operative organ transplant patient, such as a renal, heart, lung or liver transplant patient. Preferably, the patient is a post operative renal transplant patient.

As used herein "post operative organ transplant patient" refers to a patient who has received a donor organ.

Where the sample is from a post operative organ transplant patient, the sample may have been obtained from the patient 1, 2, 3, 4, 5, 6 or 7 days post transplantation.

As used herein, "DCD" is used interchangeably with the phrase "donated after circulatory death".

As used herein, "DBD" is used interchangeably with the phrase "donated after brain death".

The level of expression of the ACY-1 nucleic acid molecule can be measured in a number of ways, including: measuring the mRNA encoded by the ACY-1 nucleic acid molecule; measuring the amount of polypeptide encoded by the ACY-1 nucleic acid molecule; or measuring the activity of the polypeptide encoded by the ACY-1 nucleic acid molecule.

Any known mRNA detection methods may be used to detect the level of ACY-1 mRNA in a sample.

For example, the level of mRNA corresponding to the ACY-1 nucleic acid molecule in a sample can be determined both by in situ and by in vitro formats. ACY-1 mRNA may be detected using Southern or Northern blot analysis, polymerase chain reaction or probe arrays. In one embodiment a sample may be contacted with a nucleic acid molecule (i.e. a probe, such as a labeled probe) that can hybridize to the mRNA encoded by the ACY-1 nucleic acid molecule. The probe may be, for example, a full-length ACY-1 nucleic acid molecule, such as the nucleic acid molecule of SEQ ID NO:1, or a portion thereof, such as an nucleic acid molecule of at least 10, 15, 30, 50, 100, 250 or 500 nucleotides in length and which hybridizes under stringent conditions to an ACY-1 nucleic acid molecule.

Alternatively, the level of an ACY-1 mRNA in a sample may be evaluated with nucleic acid amplification, for example by rtPCR, ligase chain reaction, self sustained sequence replication, transcriptional amplification or any other nucleic acid amplification method, followed by the detection of the amplified molecules using techniques known in the art.

Any known protein detection methods may be used to detect the level of ACY-1 polypeptide in a sample.

Generally, protein detection methods comprise contacting an agent that selectively binds to an ACY-1 polypeptide, for example an anti-ACY-1 antibody, with a patient sample to determine the level of ACY-1 polypeptide in the sample. Preferably, the agent or antibody is labeled, for example with a detectable label. Suitable anti-ACY-1 antibodies may be polyclonal or monoclonal. An antibody fragment such as a Fab or $F(ab')_2$ may be used.

As used herein the term "labeled", refers to direct labeling of the probe or antibody by coupling (i.e., physically linking) a detectable substance to the probe or antibody, as well as indirect labeling of the probe or antibody by reactivity with a detectable substance.

The level of ACY-1 polypeptide in a sample may be determined by techniques known in the art, such as enzyme linked immunosorbent assays (ELISAs), immunoprecipitation, immunofluorescence, enzyme immunoassay (EIA), radioimmunoassay (RIA), and Western blot analysis. For in vivo detection of an ACY-1 polypeptide, a labeled anti-ACY-1 antibody may be introduced into a patient. Such an antibody can be labeled with a radioactive marker whose presence and location in a subject can be detected by standard imaging techniques.

The level of ACY-1 polypeptide in a sample may also be determined by determining the level of ACY-1 polypeptide activity in a sample.

Methods of the invention further comprise comparing the level or activity of ACY-1 in the patient sample with the level or activity of ACY-1 in a control sample or with a predetermined reference level for ACY-1.

In one embodiment, methods of the invention include contacting a control sample with a compound or agent capable of detecting an ACY-1 nucleic acid molecule, such as mRNA, or genomic DNA, and comparing the level of the ACY-1 nucleic acid molecule in the control sample with the level of ACY-1 nucleic acid molecule in the patient sample.

In another embodiment, the methods of the invention further include contacting the control sample with a compound or agent capable of detecting an ACY-1 polypeptide, and comparing the level of ACY-1 protein in the control sample with the presence of ACY-1 protein in the test sample.

As used herein "reference level" or "control", refers to a sample having a normal level of ACY-1 expression, for example a sample from a healthy subject not having or suspected of having ischaemia-reperfusion injury or alternatively a sample from the same subject that the biological test sample is obtained from, for example a sample obtained prior to organ transplantation. Alternatively, the reference level may be comprised of an ACY-1 expression level from a reference database, which may be used to generate a pre-determined cut off value, i.e. a diagnostic score that is statistically predictive of a symptom or disease or lack thereof or may be a pre-determined reference level based on a standard population sample, or alternatively, a pre-determined reference level based on a subject's base line level of expression, i.e. prior to organ transplantation.

Alternatively, predictions may be based on the normalized expression level of ACY-1. Expression levels are normalized by correcting the absolute expression level of ACY-1 in a sample by comparing its expression to the expression of a reference nucleic acid that is not a marker, e.g., an mRNA, such as an mRNA that is constitutively expressed. This normalization allows the comparison of the expression level in one sample to another sample, or between samples from different sources. This normalized expression can then optionally be compared to a reference level or control.

For example, when measuring a biomarker in urine the biomarker may be expressed as an absolute concentration or, alternatively, it may be normalized against a known urine marker, such as urine creatinine levels or urine protein levels.

In one embodiment the diagnostic or predictive methods involve determining the level of ACY-1 in a sample and determining the level of at least one further biomarker, for example a biomarker predictive or indicative of ischemia reperfusion injury or delayed graft function. Preferably, the at least one further biomarker is selected from NGAL, KIM-1, IL-18, RBP, FABP4, cystatin C and creatinine and the method further comprises detecting the level of NGAL, KIM-1, IL-18, RBP, FABP4, cystatin C and creatinine nucleic acid molecule or polypeptide in a biological test sample. Preferably, the level of the at least one further biomarker is determined using any one of the above mentioned methods.

The level of at least one further biomarker may be determined in the same biological sample or a different biological sample to the level of ACY-1.

Alternatively, the level of ACY-1 in a sample can be detected and quantified using mass spectrometry.

In one aspect the invention includes an assay device, for example a solid support such as an array or a chip, that has attached to a surface thereof a compound or agent capable of detecting an ACY-1 polypeptide or nucleic acid. Preferably, compound or agent capable of detecting an ACY-1 polypeptide is an anti-ACY-1 antibody, more preferably an ACY-1 capture antibody. In one embodiment the assay device further comprises at least one additional compound or agent for detecting a further biomarker, preferably a biomarker for kidney injury, diseases or disorders.

The inventors have identified ACY-1 as marker of ischaemia reperfusion injury or DGF. The methods of the invention allow a skilled person to make informed treatment decisions on the basis of ACY-1 levels. For example, the methods of diagnosis and prognosis described herein may further comprise a step of treating a patient or organ, on the basis of the diagnosis or prognosis. The step of treating a patient or organ may, by way of example only, be selected from: i) a step of subjecting the patient to dialysis post transplantation, e.g. the patient may be subjected to dialysis in the first week after renal transplantation; ii) a step of administering intravenous fluid to the patient, e.g. adjusting the intravenous fluid administered (i.e. increasing or decreasing the rate and volume of IVI fluid administered to a patient); and iii) a step of administering an immunosuppressant (for example a calcineurin inhibitor or mTOR inhibitor such as sirolimus) to be patient, e.g. increasing or decreasing immunosuppression or changing the type of immunosuppression therapy on the basis of ACY-1 levels.

In addition measurement of ACY-1 in the early post renal transplant period can be used to guide any potential intervention to ameliorate DGF.

Kits

The invention also includes kits for detecting the presence of ACY-1 in a biological sample. For example, the kit can include a compound or agent capable of detecting an ACY-1 polypeptide or nucleic acid in a biological sample. The compound or agent can be packaged in a suitable container. The kit can further comprise instructions for using the kit to detect ACY-1 protein or nucleic acid molecule.

In one aspect the invention provides a kit for diagnosing ischaemia-reperfusion injury or diagnosing delayed graft function in a patient comprising: a detectably labelled agent that specifically binds to an ACY-1 polypeptide or a detectably labelled agent that specifically binds to an ACY-1 nucleic acid; and ii) reagents for performing a diagnostic assay.

The agent may be an antibody or a nucleic acid molecule.

For antibody-based kits, the kit can include: (1) a first antibody (e.g., attached to a solid support) which specifically binds to an ACY-1 polypeptide corresponding to a marker of the invention; and, optionally, (2) a second, different antibody which binds to either the ACY-1 polypeptide or the first anti-ACY-1 antibody and is conjugated to a detectable agent.

For oligonucleotide-based kits, the kit can include: (1) a nucleotide probe, e.g., a detectably labeled primer, which hybridizes to an ACY-1 nucleic acid molecule or (2) a pair of primers for amplifying an ACY-1 nucleic acid molecule.

In one aspect the invention provides a kit for diagnosing ischaemia-reperfusion injury or diagnosing delayed graft function in a patient comprising an assay device comprising a first antibody (e.g., attached to a solid support) which specifically binds to an ACY-1 polypeptide corresponding to a marker of the invention; and (2) a second, different antibody which binds to either the ACY-1 polypeptide or the first anti-ACY-1 antibody and is conjugated to a detectable agent.

The kits can also include components necessary for detecting the detectable agent (e.g., an enzyme or a substrate). The kits can also contain a control sample or a series of control samples which can be assayed and compared to the test sample contained.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

1. Methods 1.1 Patient Groups and Study Design.

Patients were consented prior to undergoing renal transplantation (FIG. 1). Venous blood samples were obtained prospectively pre-transplant and longitudinally at least three times a week post-transplant (mean 14 samples/patient). Blood was collected using Z/serum clot-activator tubes (Greiner), allowed to clot for 45 minutes to 2 hours at room temperature before centrifugation at 2000 g at 20° C. for 10 min and serum aliquotted and stored at −80° C. Patient cohort 1 included 55 patients (665 samples; 47 renal transplant patients and 8 live donors), 15 of whom had DGF (based on the definition of needing dialysis in the first week after renal transplantation other than for isolated hyperkalaemia), collected in the period September 2008-July 2011, and cohort 2 included 194 patients (138 with day 1 and 177 with day 3 samples), 55 of whom had DGF, collected in the period December 2003 to March 2006. Initial biomarker discovery was carried out using serum samples from 5 patients in cohort 1 with DGF and 5 with no complications, matched clinically as far as possible, comparing samples taken pre-transplant and at day 2 post transplant (20 samples in total). Validation of the initial findings was then undertaken initially using samples from cohort 1 followed by cohort 2 with numbers being determined based on statistical power. For example, 10 DGF and 25 non-DGF patients with day 1/2 ACY-1 measurements gave a power of 80% to detect an AUC>0.8 when Bonferroni correcting a 5% significance test for 2 comparisons.

1.2 Serum Immunodepletion and Sample Preparation

The 20 serum samples in the discovery set were subjected to immunodepletion using the Multiple Affinity Reagent System 14 column (Agilent) as previously described[21]. Immunodepleted fractions were desalted and concentrated and the resulting material was digested with trypsin using a modification[21] of the filter-assisted sample preparation method (FASP)[9].

1.3 Label-Free Mass Spectrometry

After acidification to a final concentration of 0.1% TFA, peptide samples were block randomised by patient and analysed (3×2 µg injections per sample) using a Dionex UltiMate 3000 RSLCnano system connected to LTQ Orbitrap Velos mass spectrometer equipped with a Proxeon nanoelectrospray ion source[50]. Samples were injected directly onto an in-house 25 cm capillary emitter column packed with 3.5 µm Kromasil C18 media. The total acquisition time was 300 min, the major part of the gradient being 3 to 25% ACN in 0.1% formic acid at the flow rate of 0.4 µL/min. Survey MS scans were acquired in the orbitrap with the resolution set to 60,000. Up to the 20 most intense ions per scan were fragmented and analyzed in the linear trap.

1.4 Data Analysis and Statistical Methods

Label-free mass spectrometry data analysis was performed using MaxQuant (v1.1.1.25).[51] Proteins were identified using Andromeda[52] and the IPI human database (v3.75, 19 Aug. 2010) with the criteria of ≥2 peptides (at least one being unique), and proteins identified from the decoy database and known contaminants were removed. Differential expression between- and within-patient groups was assessed using non-parametric (Wilcoxon) significance tests on the changes in LFQ intensity. The false discovery rate was estimated using the q-value method.[53]

In the validation analysis, receiver operating characteristic (ROC) curves were constructed to assess predictive ability of serum ACY-1 and other markers[54]. The area under the receiver operating characteristic curve (AUC) was estimated and 95% CIs estimated from bootstrap resamples. AUCs were compared using a bootstrap significance test with the significance of differences between bootstrap AUCs assessed using a normal approximation. Multivariable logistic regression was used to assess the independent predictive ability of ACY-1 for DGF in models containing other salient predictors. The relationship between ACY-1 and other marker concentrations and dialysis-free survival was assessed using Cox proportional-hazard regression, Kaplan-Meier survival functions and the log-rank test. All statistical tests were two-sided and all analyses were undertaken in the R environment for statistical computing (R Development Core Team, Vienna, Austria).

1.5 Comparison with Other Analytes

Serum creatinine, CRP, tacrolimus, and urinary protein/creatinine ratios were measured as per clinical protocol/indication, and additionally serum creatinine and cystatin C were measured in cohort 1 at the same time points used in the study.

1.6 ELISA Development

ACY-1 concentrations were determined for the 980 serum samples in both cohorts with samples being block randomised, using an in-house developed sandwich ELISA Briefly, 96 well Nunc MaxiSorp plates (Nalge Nunc International; Rochester, N.Y.) were coated with rat anti-human ACY-1 monoclonal antibody (clone 475626; R&D Systems; Minneapolis) and ACY-1 standards (0.31-15.0 ng/mL; His-tagged recombinant ACY-1—R&D Systems) or diluted samples applied. After 2 h incubation, bound ACY-1 was detected using a goat anti-ACY-1 antibody (R&D Systems) followed sequentially by a biotinylated rabbit anti-goat IgG antibody (Sigma-Aldrich; Poole, UK), streptavidin-HRP and tetramethylbenzadine (Sigma-Aldrich). After addition of 2N sulphuric acid (Sigma-Aldrich), absorbances were determined at 450 nm (corrected at 570 nm) and ACY-1 concentrations calculated.

2. Results 2.1 Patient Groups

Examination of the patient groups (Table 1) shows similar characteristics of cohorts 1 (the discovery and initial validation group) and 2 (the larger validation group with long-term outcome data), with the exceptions of proportion of DCD transplants and the induction regimen, reflecting changing clinical practice. DGF was diagnosed in 31.9% of patients in cohort 1 and 28.4% of patients in cohort 2. Mean age and cold ischaemic time (CIT) were significantly higher in the DGF groups in each cohort, as was warm ischaemic time (WIT) in cohort 2. The 5 DGF and 5 non-DGF patients used for the initial proteomic discovery had no evidence of CNI toxicity or acute rejection and were matched as closely as possible in terms of mean age, ethnicity mix, CIT, WIT, mean HLA mismatches at the A, B and DR loci, and immunosuppression regimens, differing slightly in donor type (5 DCD in the DGF group compared with 3 DCD/2 DBD in the non-DGF group). The ten patients used in the initial discovery set were drawn from cohort 1. The 5 DGF and 5 non-DGF patients were similar in terms of mean age, ethnicity mix, CIT, WIT, mean HLA mismatches at the A, B and DR loci, induction and maintenance immunosuppression regimens and with no patient having evidence of CNI toxicity or acute rejection.

2.2 Mass Spectrometry and Candidate Biomarker Selection

Across all 20 samples (10 patients, 2 time points) used for the initial mass spectrometry screen, 553 proteins with at least 2 peptides (at least 1 of which was unique) were identified and relative quantification determined. Based on statistical significance (p<0.05), 34 candidates (including cystatin C as a proof of principle) differentiated between DGF and non-DGF groups either pre-operatively, post-operatively, or by pattern of change. Aminoacylase-1 was prioritised for further investigation, being undetectable pre-operatively in all patients but increasing markedly post-operatively, particularly in the DGF group (FIG. 2a).

Figure 2:
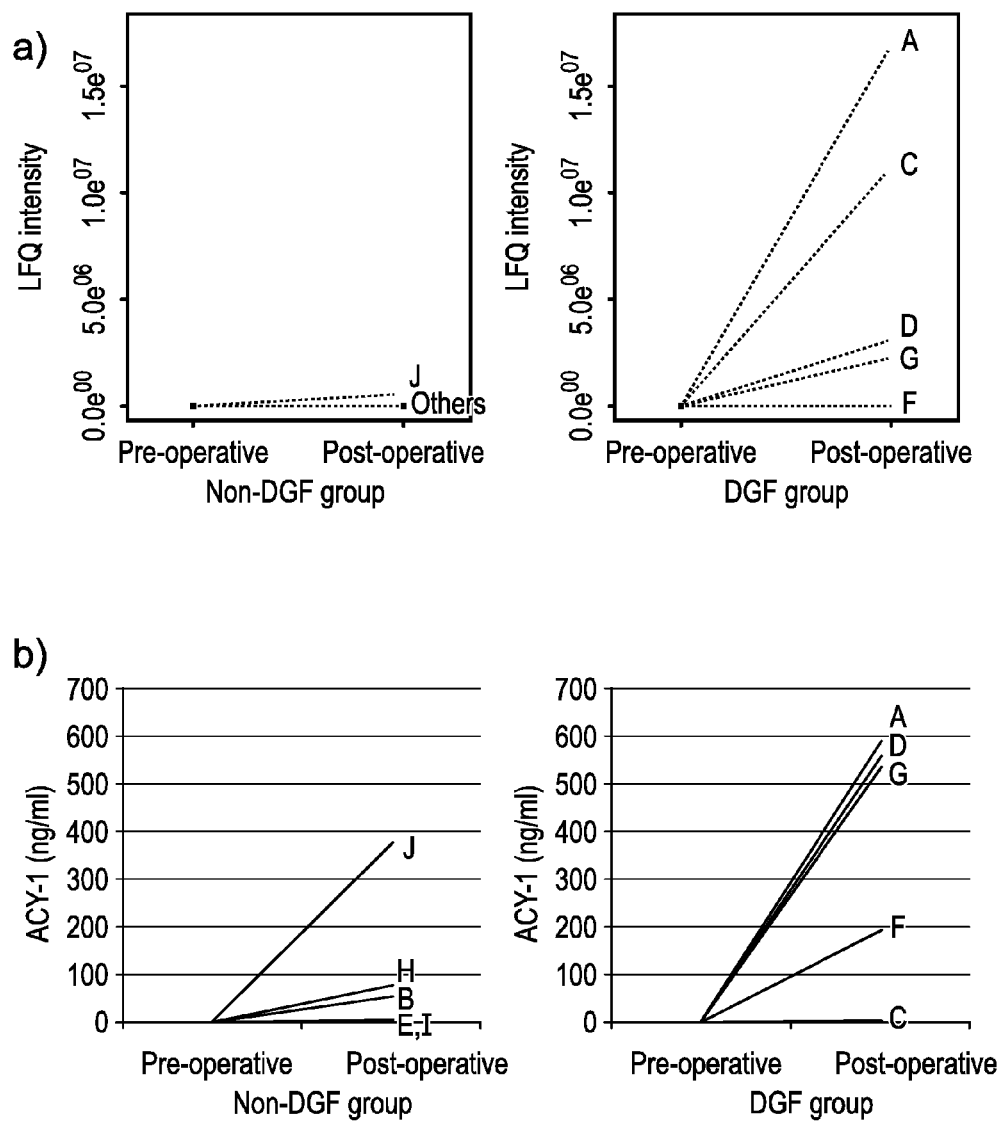
FIG. 2. Shows serum aminoacylase-1 (ACY-1) concentrations pre-operatively and on day 2 post-operatively in the delayed graft function (DGF) and non-DGF groups used for initial biomarker discovery (5 patients per group) as measured by a). mass spectrometry label-free intensity and b). subsequent ELISA for the same samples FIG. 3. Shows examples of profiles for serum aminoacylase-1 (ACY-1), creatinine and cystatin C concentrations longitudinally following renal transplantation in three patients with different clinical courses; a). uncomplicated transplant, b). delayed graft function (a patient from the subgroup showing a marked ACY-1 elevation), c). acute rejection (*) followed by 2 urinary tract infections (J). The pre-transplant concentrations are shown as day 0.

2.3 Serum Concentrations of ACY-1 in Cohort 1 and Relationship to Clinical Events Using our newly developed and validated in-house ELISA, data for serum ACY-1 broadly supported the mass spectrometry data for the discovery samples (FIG. 2). ACY-1 was undetectable (<15.6 ng/mL) in all pre-transplant samples in this set and in cohort 1 as a whole, 43/47 patients had undetectable ACY-1 pre-transplant with the remainder being <50 ng/mL and with no significant pre-transplant difference between DGF and non-DGF groups. Of the 636 longitudinal samples analysed, ACY-1 was detected in only 230 samples, predominantly in the 5 days post-transplant. Overall, of the 207 longitudinal samples in DGF patients, 138 had undetectable ACY-1 with the majority of these being pre-transplant and at >5 days post-transplant. In the non-DGF group, 268/429 longitudinal samples had undetectable concentrations of ACY-1. Similarly live donors exhibited no ACY-1 concentrations >50 ng/mL post-surgery, and the majority (10/12) of post-surgical samples had undetectable ACY-1 concentrations.

Figure 3:
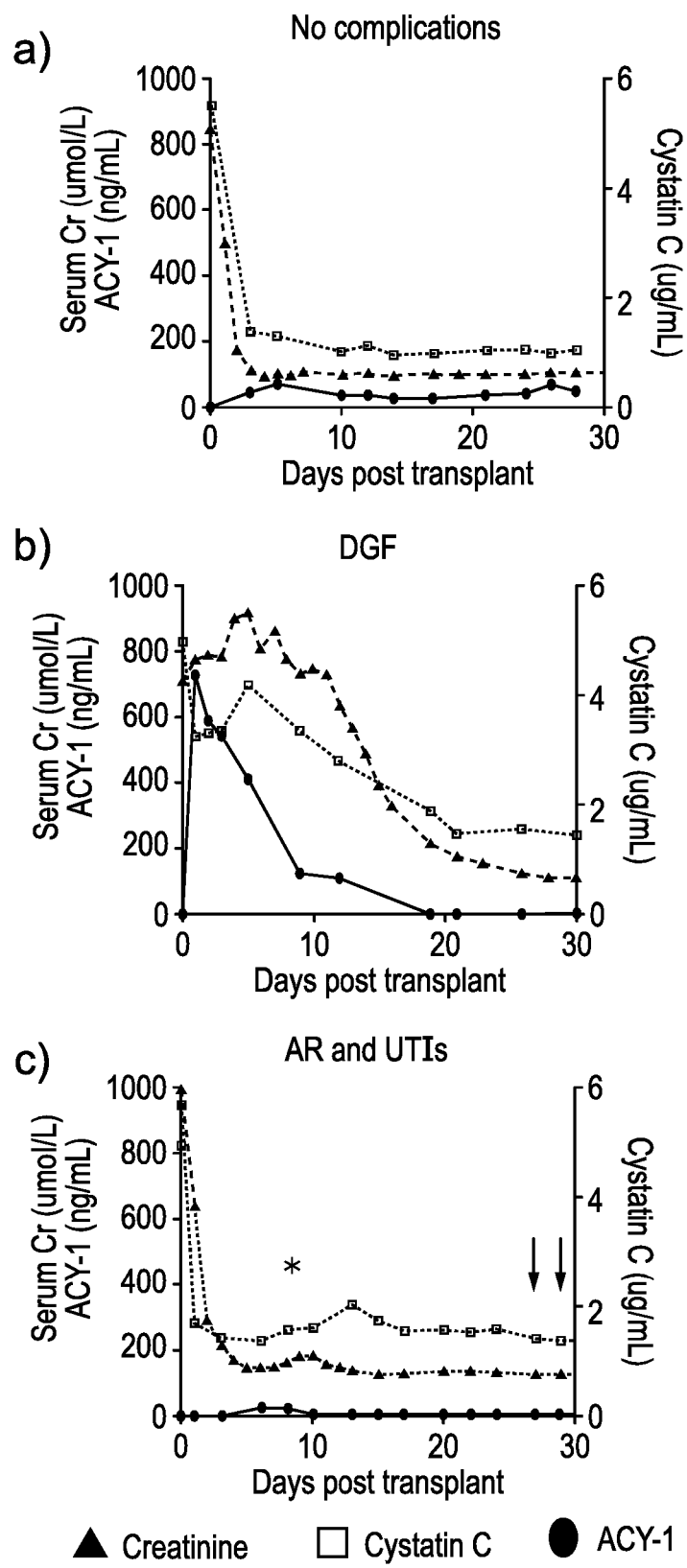

Examples of serum ACY-1 profiles with different clinical courses are shown in FIG. 3. A peak in ACY-1 concentration >200 ng/mL was observed at ≤4 days post transplantation in 10/15 patients with DGF (66.7%) but in only 6/32 (18.8%) non-DGF transplants, three of whom had an uncomplicated clinical course immediately post-transplant. Longitudinal profiles of ACY-1 concentration did not folio the trends seen in any of serum creatinine, cystatin C, CRP, tacrolimus or urinary PCR, with the exception of a peak in ACY-1 in one patient suffering from tacrolimus toxicity with an extremely high concentration of tacrolimus (trough level 33 ng/mL, intended range 9-14 ng/mL). Importantly there was no distinct peak in serum ACY-1 in patients at the time of positive mid-stream urinary cultures (n=19; ACY-1 <15.6-88.3 ng/mL), episodes of post-operative dialysis, or at the time of biopsy-proven rejection with the exception of one patient where ACY-1 concentration peaked at 260 ng/mL four days prior to biopsy, becoming undetectable by the time of the biopsy.

2.4 Serum Concentrations of ACY-1 Post-Transplant in Cohort 2 Compared with Cohort 1

Figure 4:
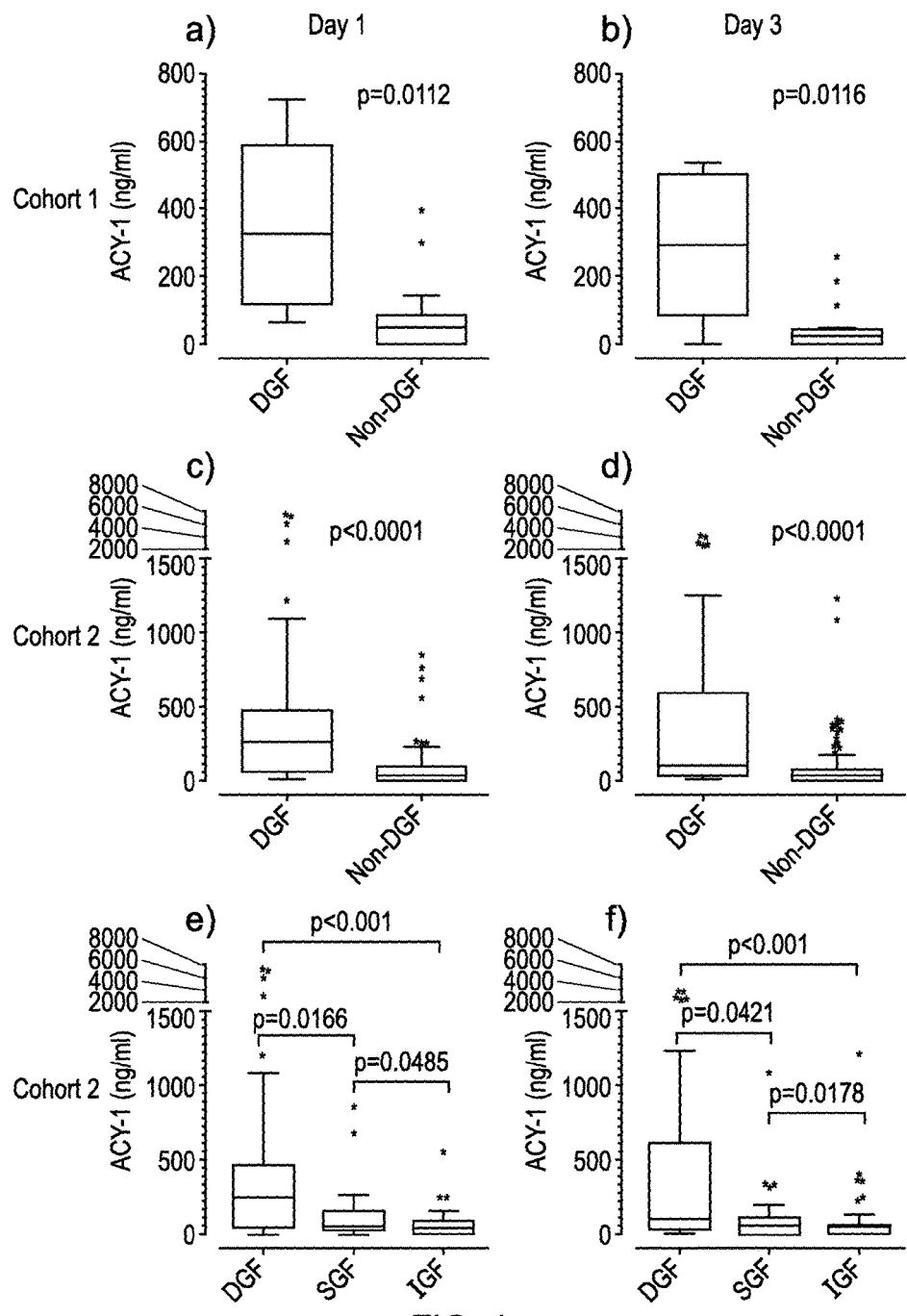
FIG. 4. Shows serum aminoacylase-1 (ACY-1) concentrations on a-d). days 1 and 3 post-transplant in the delayed graft function (DGF) and non-delayed graft function groups, for both cohort 1 and cohort 2, and e-f). on days 1 and 3 post-renal transplant in patients in cohort 2 with delayed graft function (DGF), slow graft function (SGF) and immediate graft function (IGF). Tukey's boxplots show median values and inter-quartile ranges with significant differences between the groups indicated as determined by the Mann-Whitney test.

In cohort 2 (the larger final validation set), of the 138 day 1 samples, 30 patients had undetectable serum ACY-1 concentrations (4/42 (9.5%) DGF patients, 26/96 (27.1%) non-DGF) with a similar pattern being seen (18.8% versus 42.6% respectively) for day 3 values also. In both cohorts, day 1 concentrations of ACY-1 were significantly different between the DGF and non-DGF groups although overlapping (FIG. 4$a,b$). When non-DGF patients from the larger cohort 2 were categorised on the basis of creatinine reduction ratio (CRR=(day 0 creatinine minus day 7 creatinine)/day 0 creatinine)[17,55], significant differences in day 1 serum ACY-1 (FIG. 4$c$) between patients categorised as slow graft function (SGF; CRR <0.7) and immediate graft function (IGF; CRR≥0.7) were seen with an increasing trend from IGF to SGF to DGF, demonstrating a relationship between the rate of graft function improvement and ACY-1. Similar results were also seen for day 3 serum ACY-1 concentrations.

2.5 Serum ACY-1 Associations and Predictive Utility for DGF

For initial exploratory examination of the predictive utility in cohort 1, ACY-1 and cystatin C concentrations for days 1 or 2 were combined as one time point as were those for days 3 or 4 (n=35 for each with 24 patients having samples on both time points). In cohort 1 the area under the receiver operating characteristic curve (AUC) for day 1/2 ACY-1 predicting DGF was 0.74, with corresponding figures for creatinine and cystatin C of 0.79 and 0.92 respectively. ACY-1 and cystatin C combined slightly improved the AUC to 0.94 (FIG. 5$a$). In cohort 2 the AUC for day 1 ACY-1 was 0.77 with corresponding figures for creatinine and cystatin C of 0.75 and 0.9 respectively, with the latter improving to 0.93 if combined with ACY-1 (FIG. 5$b$). Similar results were seen for day 3/4 and day 3 values for cohorts 1 and 2 respectively although the AUC for creatinine was higher at the later timepoint (FIGS. 5$c,d$). Data-derived optimum cut-points for day 1 serum ACY-1 and cystatin C in cohort 2 (Table 2) show high specificity and sensitivity respectively and the optimum cut-point from the combination of both through logistic regression provide higher sensitivity and similar specificity as is apparent through the increased Youden index[56] (0.71 vs. 0.43 and 0.64). (Table 2)

Using the larger final validation cohort 2, significant associations were observed between serum ACY-1 concentration and biopsy-proven acute tubular necrosis (ATN), transplant type, age at transplantation, CIT, total WIT, and day 1 serum creatinine and cystatin C (Table 3). On univariate analysis, days 1 and 3 serum ACY-1, cystatin C and creatinine concentrations, transplant type, WIT and total HLA mismatch were all significantly associated with the development of DGF (Table 4) A multivariable logistic regression model for the prediction of DGF was developed incorporating day 1 serum ACY-1, creatinine and cystatin C concentrations, patient age and gender, transplant type (DBD, DCD), HLA mismatch, CIT, WIT and initial steroid use. Day 1 serum ACY-1 was significant using the likelihood ratio test (LRT p=0.013; supplementary Table 4) and maintained a high, if reduced, odds ratio compared with univariate analysis. Cystatin C was the only other independent predictor of DGF in this model (p<0.0001).

Figure 8:
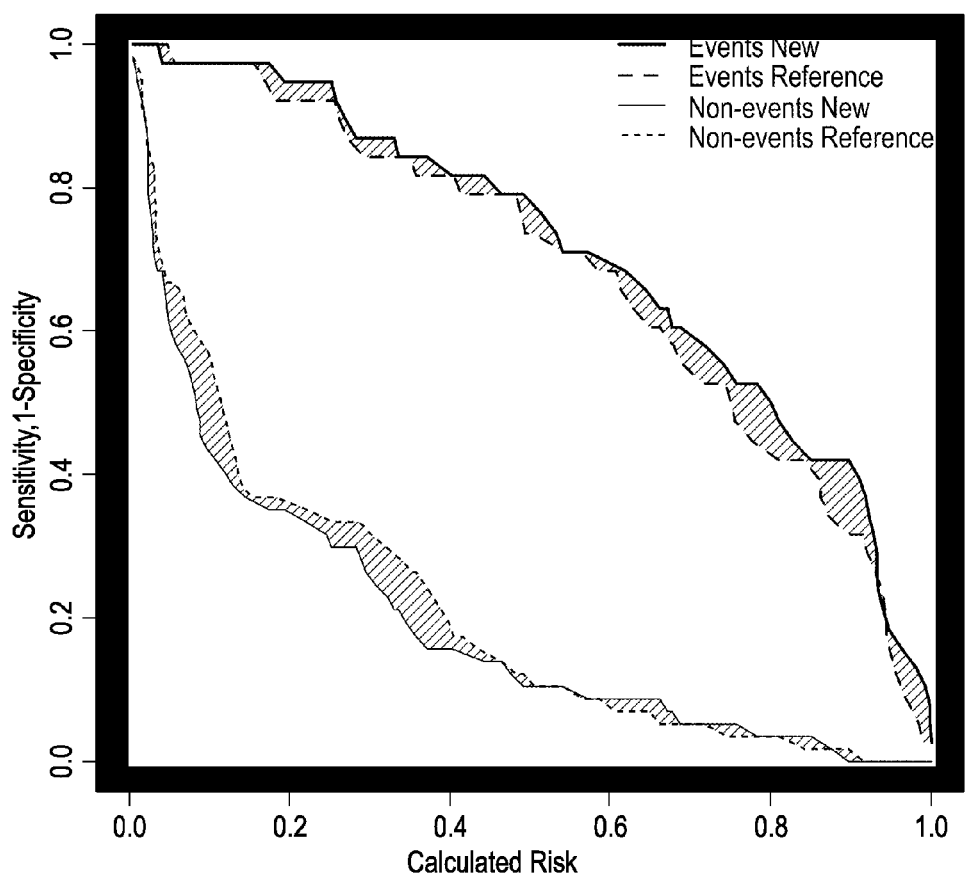
FIG. 8. Shows risk assessment plot for ACY-1 when added to reference multivariate model.

A risk assessment plot for this full multivariable model (new model) and the model without ACY-1 (reference model) are shown in FIG. 8 for patients with and without DGF. Neither model showed evidence of a lack of goodness of fit (Supplementary Table 1) nor were the AUCs significantly different as could be anticipated from bootstrap CIs (p=0.345). The greatest predictive benefit was shown to be for those patients who did not have DGF where 47.4% (95% CI 24.5-70.2%) of patients have a reduced risk according to the new model (in agreement with the high NPV in Table 2). There was also a reduction in risk for those patients with DGF and this resulted in an overall net reclassification index (NRI) with a CI that contains zero. The integrated discrimination index (IDI) for those without DGF is also reduced 0.0196 (95% CI 0.004-0.036), further demonstrating the increase in negative predictive value of ACY-1.

2.6 Serum ACY-1 and Outcome

Serum ACY-1 concentrations on day 1 post-transplant showed no correlation with length of DGF, serum creatinine, eGFR (modified MDRD), and uPCR at one year (cohorts 1 and 2). Similarly analysis of longer term follow-up data in cohort 2 showed no significant association between ACY-1 concentration on day 1 post-transplant and overall or dialysis-free survival.

Figure 9:
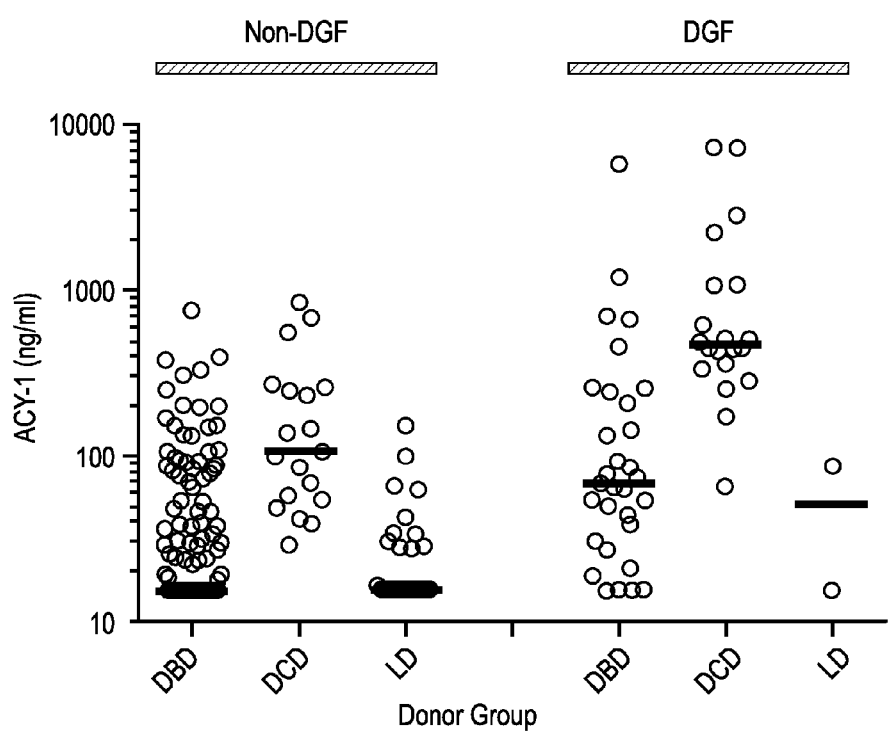
FIG. 9. Serum ACY-1 concentrations (log scale) on day 1 or 3 post-transplant for DGF and non-DGF patients in cohort 2, separated by donor type. Medians are indicated by the horizontal bar. Within the non-DGF group significant differences were seen between each donor type (p<0.001) with median values of 35.2, 107 and 15.6 ng/mL for DBD, DCD and LD respectively and similarly within the DGF group between DBD and DCD groups with median values of 70.3 and 483.2 ng/mL. Comparing between DGF and non-DGF groups, significantly higher ACY-1 concentrations were seen in patients receiving transplants from both DBD (p=0.023) and DCD (p<0.001).
Figure 10:
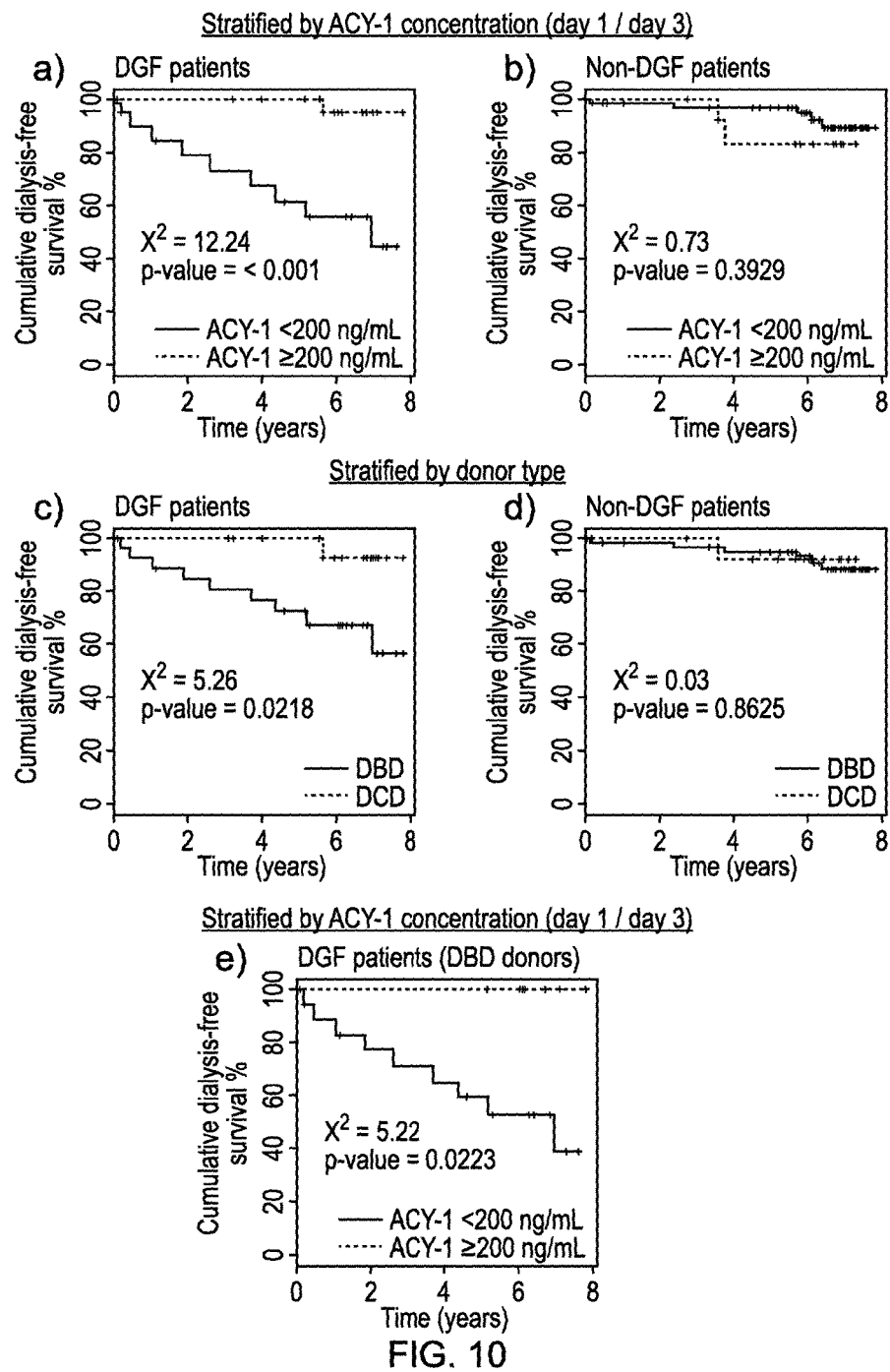
FIG. 10. Kaplan-Meier (KM) estimates of survival function for dialysis-free survival (DiFS) post-renal transplant in cohort 2 separated by salient characteristics where median follow-up was 5.93 years with a range of 0.02-7.90 years. (a) DGF and (b) non-DGF patients separated by serum concentrations of ACY-1 on day 1 post-transplant (or day 3 if no day 1 measurement was available). Numbers of events were: 1/28 (3.6%) with ACY-1≥200 and 9/24 (37.5%) with ACY-1<200 for DGF patients and 2/16 (12.5%) with ACY-1≥200 and 5/89 (5.6%) with ACY-1<200 for non-DGF patients. (c) DGF and (d) non-DGF patients separated by donor type (DCD and DBD). Numbers of events were: 1/21 (4.8%) for DCD and 9/31 (29%) for DBD within the DGF patients and 1/19 (5.3%) for DCD and 6/86 (7%) for DBD in the non-DGF group. (e) DGF patients with donor type DBD separated by ACY-1 concentration (as above). Numbers of events were: 0/9 (0%) for DBD/ACY-1≥200 and 9/22 (40.9%) for DBD/ACY-1<200. Reasons for return to dialysis included recurrent FSGF, vascular rejection and chronic scarring on biopsy.

Given the significant association of ACY-1 with DGF and the significantly increased serum concentrations seen in both DBD and DCD transplant types with DGF (FIG. 9), a sub-group analysis using the DGF group only (n=54) was undertaken and showed an association between day 1/3 (day 3 used if day 1 values unavailable) serum ACY-1 and dialysis-free survival in DGF patients (day 1 HR=0.993, 95% CI (0.988, 0.999), p=0.0174). Reflecting HRs<1, survival curves showed a significant negative association (p<0.001) between serum ACY-1 day 1/3 post-transplant in patients with DGF and risk of returning to dialysis within 5 years from transplantation which wasn't seen in the non-DGF group (FIG. 10$a,b$). The sub-division of patients with DGF into two groups based on serum ACY-1 concentration on day 1 post-transplant produces groups of similar size and although the number of events (n=10 returning to dialysis) is small, the differences remain striking. No similar associations with outcome were observed for serum cystatin C or creatinine in patients following DGF. Formal multivariable analysis was not statistically valid given the low number of events and numbers of variables but extensive examination of the clinical data detected no factors which differed between the high and low-ACY-1 sub-groups of DGF patients which could be linked to the differences in outcome with the possible exception of donor type. Within the DGF patients only, a marked difference in dialysis-free survival was seen with DBD type transplants accounting for 9/10 events (FIG. 10c,d) and within the DBD type transplant patients in the DGF group, a clear difference in outcome based on ACY-1 serum concentrations days 1/3 post-transplant was seen (FIG. 10e).

Retrospective analysis of the 15 patients with DGF in cohort 1 also suggested an association of ACY-1 with outcome. Although no graft failure and return to dialysis events have yet occurred, 3 patients appear to have failing transplants with eGFRs of 10.8, 16.1 and 13.6. Defining these as a poor outcome group and generating a contingency table classifying patients by outcome and ACY-1 (Supplementary Table 2), no evidence of a significant association (P=0.506) is seen. However, for ACY-1≥200 the odds of having a poor outcome are 1:8 whereas if ACY-1<200 the odds of a poor outcome are 2:3. A conditional MLE is calculated to be 0.215 (95% CI 0.003-5.545), suggesting an association with outcome analogous to that seen in cohort 2 and the lack of a significant test result is probably due to a combination of low power in a small sample and the more limited amount of follow-up time.

2.7 General Discussion

Although several studies report a higher frequency of DGF with DCD donor type, importantly examination of donor type confirms the lack of effect of DGF on outcomes in the DCD transplant recipient group despite prolonged periods of warm ischemia[57-59] but the detrimental effect of DGF on outcome in DBD patients[59,60]. From animal models, major systemic effects of brain death such as catecholamine release and hypotension and subsequent activation of proinflammatory mediators/cytokine response in donor organs which then provokes further host responses following transplantation have been proposed[61] Different underlying pathologies responsible for the DGF with the different donor types have been discussed with the possibility of pre-existing or pre-terminal conditions resulting in less reversible changes with DBD organs than the ATN encountered following terminal warm ischemia in DCD donors[59]. This would align with the present findings that ACY-1 is essentially a marker of repair/response to damage with those patients showing lower response having poorer outcome as can be seen in a sub-group of DBD donor type transplant patients with lower ACY-1 concentrations immediately post-transplant.

With increasing numbers of patients with end stage renal disease requiring renal transplantation, the use of organs donated after circulatory death (DCD) and from extended criteria donors is expanding. However this is associated with higher incidences of complications such as primary non-function or delayed graft function which can have significant impacts on clinical and economic outcomes. A significant number of grafts from such donors are discarded following retrieval and prior to transplantation due to being assessed as being of insufficient quality. Decisions regarding discard are largely based on subjective assessment and clinical experience and more objective measures are needed. Kidneys procured from deceased donors, both donor after brain death (DBD) and DCD, are flushed in situ with a cold preservation solution prior to removal and storage on ice in a preservation medium. Increasingly, hypothermic machine perfusion involving recirculating preservation fluid through the renal artery for 4-12 hours is being used, and is reported to result in better outcomes although evidence is conflicting. Measures of perfusion dynamics such as flow resistance and perfusate concentrations of factors such as glutathione S-transferase, lactate dehydrogenase, and heart-type fatty acid binding protein have been examined as potential indicators of graft viability but studies are few and such markers do not appear to be reliable predictors of outcome.

Preliminary results show that ACY-1, in addition to be detectable in serum post-transplant and particularly associated with some patients with DGF, can also be measured in machine perfusate fluid from kidneys prior to transplant. Preliminary results show concentrations similar to those in serum and with potentially higher levels in DCD grafts than DBD. This therefore offers the potential to be able to measure ACY-1 in perfusate fluid prior to use of the organ in transplantation and together with other markers may provide some indication of damage/repair processes which would be important in determining graft quality and/or outcome of the transplant.

The finding of peptides in the mass spectrometric analysis of tryptic digests perfusate fluid derived from ACY-2 and ACY-3 in addition to ACY-1 may mean that those ACY-2 and ACY-3 may also be of value as potential biomarkers.

TABLE 1

Details for the delayed graft function (DGF) and non-DGF patients in cohorts 1 and 2. Details of biopsies performed, and other post-operative events (e.g. urinary tract infections, UTIs) were collected along with serum creatinine (SCr), tacrolimus concentrations, C-reactive protein (CRP) concentrations, and urinary protein/creatinine ratios (uPCRs). In addition 8 live donors were included in the study to check for the effects of surgery (mean age 44.0 ± 12.3, 37.5% male).

|  | Cohort 1 | | | Cohort 2 | | |
| --- | --- | --- | --- | --- | --- | --- |
|  | DGF | non-DGF | p-value | DGF | non-DGF | p-value |
| Number of patients, and subgroups | n = 15 total<br>6 biopsied:<br>4 acute rejection<br>2 ATN<br>9 not biopsied:<br>5 calcineurin inhibitor toxicity, 4 assumed ATN | n = 32 total<br>8 biopsied:<br>6 acute rejection<br>2 mild tubular injury<br>24 not biopsied:<br>12 uncomplicated<br>4 post-transplant UTIs<br>8 calcineurin inhibitor toxicity | N/A | n = 55 total<br>40 biopsied:<br>26 ATN<br>8 rejection<br>6 both ATN and acute rejection<br>15 not biopsied:<br>all assumed ATN | n = 139<br>16 biopsied:<br>11 ATN<br>5 ATN and acute rejection<br>123 not biopsied:<br>uncomplicated transplants | N/A |

TABLE 1-continued

Details for the delayed graft function (DGF) and non-DGF patients in cohorts 1 and 2. Details of biopsies performed, and other post-operative events (e.g. urinary tract infections, UTIs) were collected along with serum creatinine (SCr), tacrolimus concentrations, C-reactive protein (CRP) concentrations, and urinary protein/creatinine ratios (uPCRs). In addition 8 live donors were included in the study to check for the effects of surgery (mean age 44.0 ± 12.3, 37.5% male).

|  |  | Cohort 1 | | | Cohort 2 | | |
|---|---|---|---|---|---|---|---|
|  |  | DGF | non-DGF | p-value | DGF | non-DGF | p-value |
| Cause of ESRD (%) | Chronic pyelonephritis | 0.0 | 18.8 | 0.573 | 14.5 | 12.2 | 0.719 |
|  | Diabetes | 6.7 | 3.1 |  | 12.7 | 10.1 |  |
|  | Glomerulonephritis | 33.3 | 31.3 |  | 32.7 | 30.9 |  |
|  | Hypertension | 6.7 | 12.5 |  | 5.5 | 10.8 |  |
|  | Inherited | 26.7 | 12.5 |  | 14.5 | 10.8 |  |
|  | Other | 20.0 | 15.6 |  | 7.3 | 5.0 |  |
|  | Unknown | 6.7 | 6.3 |  | 12.7 | 20.1 |  |
| Ethnicity (%) | Asian | 6.7 | 6.3 | 0.997 | 20.0 | 8.6 | 0.113 |
|  | Black/African/Caribbean | 6.7 | 6.3 |  | 1.8 | 1.4 |  |
|  | Caucasian | 86.7 | 87.5 |  | 58.2 | 61.9 |  |
|  | Unknown | 0.0 | 0.0 |  | 18.2 | 28.1 |  |
| Transplant number (%) | 1 | 86.7 | 78.1 | 0.807 | 80.0 | 90.6 | 0.247 |
|  | 2-4 | 13.3 | 21.9 |  | 18.2 | 7.9 |  |
|  | Unknown | 0 | 0 |  | 1.8 | 1.4 |  |
| Pre-emptive (%) | N | 100.0 | 78.1 | 0.128 | 96.4 | 92.8 | 0.338 |
|  | Y | 0.0 | 21.9 |  | 1.8 | 6.5 |  |
|  | Unknown | 0 | 0 |  | 1.8 | 0.7 |  |
| Mean time (months) on dialysis at transplantation ± sd* |  | 32.8 ± 20.7 | 32.2 ± 25.0 | 0.941 | 54.6 ± 40.4 | 36.5 ± 36.4 | <0.001 |
| Mean age (years) ± sd |  | 52.4 ± 12.1 | 40.6 ± 14.1 | 0.007 | 50 ± 13.9 | 46.2 ± 14.9 | 0.046 |
| Gender | % male | 73.3 | 59.3 | 0.547 | 37.0 | 62.6 | 0.002 |
| Transplant types | % DBD | 20.0 | 28.1 | 0.006 | 57.4 | 61.9 | <0.001 |
|  | % DCD | 80.0 | 34.3 | (0.123)# | 38.9 | 13.7 |  |
|  | % LD | 0.0 | 37.5 |  | 3.7 | 24.5 |  |
| Induction (%) | Alemtuzumab | 26.7 | 31.2 | 0.983 | 0 | 0 | N/A |
|  | Basiliximab | 73.3 | 68.7 |  | 100 | 100 |  |
| Maintenance steroids used (%) |  | 26.7 | 21.9 | 0.994 | 14.8 | 10.1 | 0.527 |
| Mean ischaemic time ± sd | Cold (h:min) | 16:06 ± 03:11 | 10:24 ± 06:08 | 0.002 | 16:42 ± 04:48 | 13:48 ± 08:18 | 0.019 |
|  | Warm (min) | 40 ± 13 | 39 ± 9 | 0.782 | 49.2 ± 19.1 | 36.9 ± 13.6 | <0.001 |
| Mean total HLA mismatch ± sd |  | 3.3 ± 1.0 | 2.6 ± 1.8 | 0.127 | 2.4 ± 1.3 | 2.0 ± 1.4 | 0.096 |

DBD—donations after brain death, DCD—donations after circulatory death, LD—live donors, ATN—acute tubular necrosis.
P-values are provided for differences between the DGF and non-DGF groups in each cohort.
*excludes pre-emptive transplants, for second and subsequent transplants, total time on dialysis aggregated
p value if LD excluded as rare in DGF

TABLE 2

Estimates and 95% confidence intervals for measures of diagnostic accuracy for ACY-1, cystatin C, serum creatinine and combined serum ACY-1 and cystatin C for optimal cut-offs as determined in cohort 2 data for day 1 measurements (for serum Cr the additional condition that specificity was >50% was applied)

| ACY-1 | | | |
|---|---|---|---|
| (cut-off 200 ng/mL) | Estimate | LCI | UCI |
| Sensitivity | 54.76 | 39.71 | 69.81 |
| Specificity | 88.54 | 82.17 | 94.91 |
| PPV* | 67.65 | 51.92 | 83.37 |
| NPV** | 81.73 | 74.30 | 89.16 |
| OR*** | 9.35 | 3.90 | 22.40 |
| Youden index | 0.43 | | |

| Cystatin C | | | |
|---|---|---|---|
| (cut-off 3.3 µg/mL) | Estimate | LCI | UCI |
| Sensitivity | 87.18 | 76.69 | 97.67 |
| Specificity | 76.40 | 67.58 | 85.23 |
| PPV | 61.82 | 48.98 | 74.66 |
| NPV | 93.15 | 87.36 | 98.95 |
| OR | 22.02 | 7.64 | 63.47 |
| Youden index | 0.64 | | |

| Serum Creatinine | | | |
|---|---|---|---|
| (cut-off 550 µmol/L) | Estimate | LCI | UCI |
| Sensitivity | 79.63 | 68.89 | 90.37 |
| Specificity | 55.56 | 46.88 | 64.23 |
| PPV | 43.43 | 33.67 | 53.20 |
| NPV | 86.42 | 78.96 | 93.88 |
| OR | 4.89 | 2.31 | 10.35 |
| Youden index | 0.35 | | |

| ACY-1 + Cystatin C | | | |
|---|---|---|---|
| (cut-off probability 0.2) | Estimate | LCI | UCI |
| Sensitivity | 92.31 | 83.94 | 100 |
| Specificity | 78.65 | 70.14 | 87.16 |
| PPV | 65.45 | 52.89 | 78.02 |
| NPV | 95.89 | 91.34 | 100 |
| OR | 44.21 | 12.26 | 100 |
| Youden index | 0.71 | | |

*positive predictive value
**negative predictive value
***odds ratio

TABLE 3

Associations between day 1 serum ACY-1 concentration and relevant variables in cohort 2 (n = 138 with day 1 samples).

| Characteristic | Subgroup | N | Median (range) | p-value* |
|---|---|---|---|---|
| Gender | M | 90 | 43.4 (15.6, 7324.5) | |
| | F | 48 | 74.5 (15.6, 7207.2) | 0.1277 |
| Age at transplantation (years) | — | 138 | 0.30 | 0.0003 |
| Transplant type | DBD | 79 | 48.3 (15.6, 5905.3) | |
| | DCD | 29 | 365.6 (29.3, 7324.5) | |
| | LD | 30 | 15.6 (15.6, 156.1) | <0.0001 |
| CIT (mins) | — | 138 | 0.25 | 0.0033 |
| Total WIT (mins) | — | 138 | 0.53 | <0.0001 |
| Total HLA mismatch | 0, 1 & 2 | 82 | 50.7 (15.6, 5905.3) | |
| | 3, 4, 5 & 6 | 56 | 76.2 (15.6, 7324.5) | 0.1261 |
| Initial steroid use | Y | 15 | 72.3 (15.6, 1094.2) | |
| | N | 123 | 53.2 (15.6, 7324.5) | 0.9397 |
| DGF | Y | 42 | 253.7 (15.6, 7324.5) | |
| | N | 96 | 33.6 (15.6, 864.1) | <0.0001 |
| Biopsy proven Acute Rejection (AR) | Y | 11 | 66.3 (15.6, 1094.2) | |
| | N | 127 | 53.4 (15.6, 7324.5) | 0.6354 |
| Biopsy proven Acute Tubular Necrosis (ATN) | Y | 29 | 143.9 (15.6, 7324.5) | |
| | N | 109 | 44.0 (15.6, 1225.1) | 0.0007 |
| Both ATN and AR on biopsy | Y | 4 | 140.8 (18.8, 511.1) | |
| | N | 134 | 53.7 (15.6, 7324.5) | 0.5965 |
| Serum creatinine day 1 (μmol/L) | — | 130 | 0.25 | 0.0050 |
| Serum cystatin C day 1 (μg/mL) | — | 128 | 0.41 | <0.0001 |

Transplant types: DBD—Donation after Brain Death; DCD—Donation after Cardiac Death; LD—Live Donor; CIT—Cold Ischaemic Time; WIT—Warm Ischaemic Time; HLA—Human Leucocyte Antigen; "Initial steroid use" refers to whether patients received maintenance oral prednisolone as part of their initial daily immunosuppression regime.; DGF—Delayed Graft Function; Biopsy results—a total of 32 of these 138 patients had biopsies and therefore the N category for the biopsy results includes those who did not undergo a biopsy.
*Spearman's rank correlation coefficient/p-value if single variable, or p-value from Wilcoxon Mann-Whitney test or Kruskal Wallis test if comparing 2 or 3 independent subgroups respectively

TABLE 4

Univariate and multivariable analysis of factors associated with delayed graft function in cohort 2 as determined by logistic regression.

| Factor | Level | Univariate | | | Multivariable | | |
|---|---|---|---|---|---|---|---|
| | | Odds ratio | 95% CI | p-value | Odds ratio | 95% CI | p-value |
| Gender | Male | 1 | | | 1 | | |
| | Female | 0.901 | (0.456, 1.780) | 0.7645 | 0.888 | (0.223, 3.377) | 0.8612 |
| Age at transplantation (years) | — | 1.015 | (0.992, 1.039) | 0.2085 | 1.000 | (0.959, 1.043) | 0.9871 |
| Transplant type | DBD | 1 | | | 1 | | |
| | DCD | 3.066 | (1.457, 6.453) | 0.0032 | 0.730 | (0.086, 6.181) | 0.7724 |
| CIT (mins) | — | 1 | (0.998, 1.001) | 0.5720 | 1.000 | (0.997, 1.003) | 0.8496 |
| Total WIT (mins) | — | 1.040 | (1.017, 1.064) | 0.0007 | 1.043 | (0.991, 1.097) | 0.1040 |
| Total HLA mismatch | 0, 1 & 2 | 1 | | | 1 | | |
| | 3, 4, 5 & 6 | 2.500 | (1.255, 4.979) | 0.0091 | 1.679 | (0.415, 6.798) | 0.4676 |
| Initial steroid use | N | 1 | | | 1 | | |
| | Y | 1.239 | (0.424, 3.618) | 0.6949 | 2.465 | (0.290, 20.99) | 0.4089 |
| Serum ACY-1 day 1 (per increase 1 μg/mL) | — | 31.17 | (3.400, 285.7) | 0.0023 | 13.82 | (1.321, 434.9) | 0.0115 |
| Serum creatinine day 1 (per increase 1 μmol/L) | — | 1.004 | (1.002, 1.006) | <0.0001 | 1.001 | (0.997, 1.004) | 0.7526 |
| Serum cystatin C day 1 (per increase 1 μg/mL) | — | 5.536 | (2.775, 11.05) | <0.0001 | 6.865 | (2.678, 17.60) | <0.0001 |

Transplant types:
DBD—Donation after Brain Death;
DCD—Donation after Cardiac Death;
CIT—Cold Ischaemic Time;
WIT—Warm Ischaemic Time;
HLA—Human Leucocyte Antigen;
"Initial steroid use" refers to whether patients received maintenance oral prednisolone as part of their initial daily immunosuppression regime.
P-values from Wald test for all variables other than multivariable ACY-1 day 1 where LRT p-value is more appropriate due to larger relative odds ratio.

3. Serum ACY-1 Levels in Heart and Lung Samples

In patients following heart or lung transplants, serum aminoacylase-1 was observed to be elevated in many but not all patients at various time intervals post-surgery with very significantly elevated levels in at least 3 patients (Tables 5 and 6). This may indicate specific damage such as ischaemia-reperfusion injury in the transplanted tissue with significant ischaemic times in such patients. although the significance with respect to outcome is not clear yet and requires further longitudinal studies.

TABLE 5

Heart Tx

| Sample | Days Post Tx | Serum A Concentration (ng/mL) |
| --- | --- | --- |
| T20778 | 7 | 67.52 |
| T20761 | 5 | 35.68 |
| T20279 | 7 | 55.70 |
| T19748 | 8 | 17.41 |
| T19598 | 7 | 104.37 |
| T19325 | 7 | 56.49 |
| T18340 | 8 | <7.8 |
| T17068 | 7 | 28.38 |
| T16946 | 8 | 104.57 |
| T16414 | 8 | 24.58 |
| T15575 | 8 | >750.0 |
| T15259 | 2 | 42.66 |
| T14440 | 5 | 109.83 |

TABLE 6

Lung Tx

| Sample | Days Post Tx | Serum A Concentration (ng/mL) |
| --- | --- | --- |
| T19537 | 2 | 29.03 |
| T19134 | 8 | 46.97 |
| T2863 | 4 | 25.77 |
| T1659 | 6 | <7.8 |
| T1206 | 2 | <7.8 |
| Y94-00488 | 3 | >750.0 |
| Y92-03624 | 3 | 138.10 |
| C60192 | 3 | 336.84 |
| Y93-02141 | 7 | 44.29 |

SUPPLEMENTARY TABLE 1

Summary statistics for model improvement metrics when ACY-1 is added to reference logistic regression model. Metrics are: the deviance-based test of goodness of fit, the category-free net reclassification improvement (NRI) and integrated discrimination improvement (IDI) for those with and without an event, i.e. DGF. IS and IP are the integrated sensitivity and 1-specificity. AUC is the area under the receiver operating characteristic curve and associated DeLong test for comparing curves. All CIs are determined using 2000 bootstrap resamples.

| | |
| --- | --- |
| Total (n) | 95 |
| Events (n) | 38 |
| Non-events (n) | 57 |
| Goodness of fit | |
| Goodness of fit (null model P) | 0.7648 |
| Goodness of fit (alt model P) | 0.8828 |
| NRI and summary statistics | |
| NRI events | −0.3158 (−0.6236, −0.008) |
| NRI non-events | 0.4737 (0.2451, 0.7022) |
| NRI | 0.1579 (−0.2237, 0.5395) |
| IDI and summary statistics | |
| IDI events | 0.0294 (−0.0183, 0.0772) |
| IDI non-events | 0.0196 (0.0037, 0.0355) |
| IDI | 0.0098 (−0.0407, 0.0604) |
| IS (null model) | 0.6778 (0.5899, 0.7657) |
| IS (alt model) | 0.7055 (0.6180, 0.7930) |
| IP (null model) | 0.2072 (0.1504, 0.2641) |
| IP (alt model) | 0.1884 (0.1311, 0.2458) |
| AUC | |
| AUC (null model) | 0.8984 (0.8375, 0.9594) |
| AUC (alt model) | 0.9109 (0.8544, 0.9674) |
| difference (P) | 0.3450 |

SUPPLEMENTARY TABLE 2

Contingency table classifying graft outcome against day 1 serum ACY-1 concentration in the patients with DGF in cohort 1.

| | Good outcome | Poor outcome |
| --- | --- | --- |
| ACY-1 < 200 | 3 | 2 |
| ACY-1 ≥ 200 | 8 | 1 |

Although of the 15 patients with DGF in cohort 1, no graft failure and return to dialysis events have yet occurred, 3 patients appear to have failing transplants with eGFRs of 10.8, 16.1 and 13.6, 2 of whom are being prepared for a second transplant. Defining these as a poor outcome group and with the remaining patients in the cohort all having eGFR>30 at latest measurement and being classified as good outcome, a contingency table classifying patient by outcome and their peak ACY-1 concentration within days 1 to 3 is shown. Note that one patient did not have an ACY-1 measurement on days 1-3 hence only 14 patients are included. The Fisher's exact test suggests no evidence of a significant association between ACY-1 concentration and outcome (P=0.506). However, if you have ACY-1≥200 the odds of having a poor outcome are 1/8 whereas if ACY-1<200 the odds of a poor outcome are 2/3. This equates to an (unconditional MLE) odds ratio of 2/16. However, given the small sample size a conditional MLE is more appropriate and is calculated to be 0.215 (95% CI 0.003-5.545). This suggests that this data shows an association with outcome analogous to that seen in cohort 2 and the lack of a significant test result is probably due to a combination of low power in a small sample and the limited amount of follow-up time.

REFERENCES

1. Port, F. K., Wolfe, R. A., Mauger, E. A., Berling, D. P. & Jiang, K. Comparison of survival probabilities for dialysis patients vs cadaveric renal transplant recipients. *J.A.M.A.* 270, 1339-1343 (1993).
2. Wolfe, R. A., et al. Comparison of mortality in all patients on dialysis, patients on dialysis awaiting transplantation, and recipients of a first cadaveric transplant. *N. Engl. J. Med.* 341, 1725-1730 (1999).
3. de Wit, G. A., Ramsteijn, P. G. & de Charro, F. T. Economic evaluation of end stage renal disease treatment. *Health Policy* 44, 215-232 (1998).
4. Kontodimopoulos, N. & Niakas, D. An estimate of lifelong costs and QALYs in renal replacement therapy based on patients' life expectancy. *Health Policy* 86, 85-96 (2008).
5. Tapiawala, S. N., et al. Delayed graft function and the risk for death with a functioning graft. *J. Am. Soc. Nephrol.* 21, 153-161 (2010).
6. Akkina, S. K., et al. Similar outcomes with different rates of delayed graft function may reflect center practice, not center performance. *Am. J. Transplant.* 9, 1460-1466 (2009).
7. Roels, L., et al. Inferior outcome of cadaveric kidneys preserved for more than 24 hr in histidine-tryptophan-ketoglutarate solution. Leuven Collaborative Group for Transplantation. *Transplantation* 66, 1660-1664 (1998).
8. Chang, S. H., Russ, G. R., Chadban, S. J., Campbell, S. B. & McDonald, S. P. Trends in kidney transplantation in Australia and New Zealand, 1993-2004. *Transplantation* 84, 611-618 (2007).

9. Siedlecki, A., Irish, W. & Brennan, D. C. Delayed graft function in the kidney transplant. *Am. J. Transplant.* 11, 2279-2296 (2011).
10. Keitel, E., et al. Renal transplants using expanded cadaver donor criteria. *Ann. Transplant.* 9, 23-24 (2004).
11. Halloran, P. F., et al. Early function as the principal correlate of graft survival. A multivariate analysis of 200 cadaveric renal transplants treated with a protocol incorporating antilymphocyte globulin and cyclosporine. *Transplantation* 46, 223-228 (1988).
12. Snyder, J. J., Kasiske, B. L., Gilbertson, D. T. & Collins, A. J. A comparison of transplant outcomes in peritoneal and hemodialysis patients. *Kidney Int.* 62, 1423-1430 (2002).
13. Sola, R., Alarcon, A., Jimenez, C. & Osuna, A. The influence of delayed graft function. *Nephrol. Dial. Transplant.* 19 Suppl 3, iii32-37 (2004).
14. Yarlagadda, S. G., Coca, S. G., Formica, R. N., Jr., Poggio, E. D. & Parikh, C. R. Association between delayed graft function and allograft and patient survival: a systematic review and meta-analysis. *Nephrol. Dial. Transplant.* 24, 1039-1047 (2009).
15. Muhlberger, I., Perco, P., Fechete, R., Mayer, B. & Oberbauer, R. Biomarkers in renal transplantation ischemia reperfusion injury. *Transplantation* 88, S14-19 (2009).
16. Smith, M. P., Banks, R. E., Wood, S. L., Lewington, A. J. & Selby, P. J. Application of proteomic analysis to the study of renal diseases. *Nat. Rev. Nephrol.* 5, 701-712 (2009).
17. Hall, I. E., et al. IL-18 and urinary NGAL predict dialysis and graft recovery after kidney transplantation. *J. Am. Soc. Nephrol.* 21, 189-197 (2010).
18. Schwarz, C., et al. The contribution of adhesion molecule expression in donor kidney biopsies to early allograft dysfunction. *Transplantation* 71, 1666-1670 (2001).
19. Hall, I. E., Doshi, M. D., Poggio, E. D. & Parikh, C. R. A comparison of alternative serum biomarkers with creatinine for predicting allograft function after kidney transplantation. *Transplantation* 91, 48-56 (2011).
20. Anderson, N. L. & Anderson, N. G. The human plasma proteome: history, character, and diagnostic prospects. *Mol. Cell. Proteomics* 1, 845-867 (2002).
21. Smith, M. P., et al. A systematic analysis of the effects of increasing degrees of serum immunodepletion in terms of depth of coverage and other key aspects in top-down and bottom-up proteomic analyses. Proteomics Clin. Appl. 5, 561 (2011).
22. Cook, R. M., Burke, B. J., Buchhagen, D. L., Minna, J. D. & Miller, Y. E. Human aminoacylase-1. Cloning, sequence, and expression analysis of a chromosome 3p21 gene inactivated in small cell lung cancer. *J. Biol. Chem.* 268, 17010-17017 (1993).
23. Perrier, J., Durand, A., Giardina, T. & Puigserver, A. Catabolism of intracellular N-terminal acetylated proteins: involvement of acylpeptide hydrolase and acylase. *Biochimie* 87, 673-685 (2005).
24. Lindner, H., et al. The distribution of aminoacylase I among mammalian species and localization of the enzyme in porcine kidney. *Biochimie* 82, 129-137 (2000).
25. Sass, J. O., et al. Mutations in ACY1, the gene encoding aminoacylase 1, cause a novel inborn error of metabolism. *Am. J. Hum. Genet.* 78, 401-409 (2006).
26. Yamauchi, A., et al. Tissue distribution of and species differences in deacetylation of N-acetyl-L-cysteine and immunohistochemical localization of acylase I in the primate kidney. *J. Pharmacy Pharmacol.* 54, 205-212 (2002).
27. Miller, Y. E. & Kao, B. Monoclonal antibody based immunoassay for human aminoacylase-1. *J. Immunoassay* 10, 129-152 (1989).
28. Lindner, H. A., Tafler-Naumann, M. & Rohm, K. H. N-acetylamino acid utilization by kidney aminoacylase-1. *Biochimie* 90, 773-780 (2008).
29. Sommer, A., et al. The molecular basis of aminoacylase 1 deficiency. *Biochim. Biophys. Acta* 1812, 685-690 (2011).
30. Zhong, Y., et al. Genome-wide analysis identifies a tumor suppressor role for aminoacylase 1 in iron-induced rat renal cell carcinoma. *Carcinogenesis* 30, 158-164 (2009).
31. Miller, Y. E., Minna, J. D. & Gazdar, A. F. Lack of expression of aminoacylase-1 in small cell lung cancer. Evidence for inactivation of genes encoded by chromosome 3p. *J Clin Invest* 83, 2120-2124 (1989).
32. Abu Jawdeh, B. G. & Rabb, H. Delayed kidney allograft function—what does it tell us about acute kidney injury? *Contrib. Nephrol.* 174, 173-181 (2011).
33. Klawitter, J., et al. Association of immunosuppressant-induced protein changes in the rat kidney with changes in urine metabolite patterns: a proteo-metabonomic study. *J. Proteome Res.* 9, 865-875 (2010).
34. Asif, A. R., et al. Proteins identified as targets of the acyl glucuronide metabolite of mycophenolic acid in kidney tissue from mycophenolate mofetil treated rats. *Biochimie* 89, 393-402 (2007).
35. Kotsch, K., et al. Novel markers in zero-hour kidney biopsies indicate graft quality and clinical outcome. *Transplantation* 90, 958-965 (2010).
36. Dikow R, Becker L E, Schaier M, et al. In renal transplants with delayed graft function chemokines and chemokine receptor expression predict long-term allograft function. *Transplantation* 2010; 90: 771-776.
37. Halawa, A. The early diagnosis of acute renal graft dysfunction: a challenge we face. The role of novel biomarkers. *Ann. Transplant.* 16, 90-98 (2011).
38. Malyszko, J. Biomarkers of acute kidney injury in different clinical settings: a time to change the paradigm? *Kidney and Blood Pressure Research* 33, 368-382 (2010).
39. Schroppel, B., et al. Tubular expression of KIM-1 does not predict delayed function after transplantation. *J. Am. Soc. Nephrol.* 21, 536-542 (2010).
40. Parikh, C. R., et al. Urine NGAL and IL-18 are predictive biomarkers for delayed graft function following kidney transplantation. *Am. J. Transplant.* 6, 1639-1645 (2006).
41. Hollmen, M. E., Kyllonen, L. E., Inkinen, K. A., Lalla, M. L. & Salmela, K. T. Urine neutrophil gelatinase-associated lipocalin is a marker of graft recovery after kidney transplantation. *Kidney Int.* 79, 89-98 (2011).
42. Zhang, Z., Lu, B., Sheng, X. & Jin, N. Cystatin C in prediction of acute kidney injury: a systemic review and meta-analysis. *Am. J. Kidney Dis.* 58, 356-365 (2011).
43. Supavekin, S., et al. Differential gene expression following early renal ischemia/reperfusion. *Kidney Int.* 63, 1714-1724 (2003).
44. Park S W, Kim M, Kim M, et al. Sphingosine kinase 1 protects against renal ischaemia-reperfusion injury in mice by sphingosine-1-phosphate) receptor activation. *Kidney Int* 2011; 2011: 1315-1327.

45. Bajwa A, Jo S K, Ye H, et al. Activation of sphingosine-1-phosphate 1 receptor in the proximal tubule protects against ischaemia-reperfusion injury. *J Am Soc Nephrol* 2010; 21: 955-965.
46. Sola A, Weigert A, Jung M, et al. Sphingosine-1-phosphate signalling induces the production of Lcn-2 by macrophages to promote kidney regeneration. *Journal of Pathology* 2011; 225: 597-608.
47. Mas, V. R., et al. Pretransplant transcriptome profiles identify among kidneys with delayed graft function those with poorer quality and outcome. *Mol. Med.* 17, 1311-1322 (2011).
48. Maceyka, M., Nava, V. E., Milstien, S. & Spiegel, S. Aminoacylase 1 is a sphingosine kinase 1-interacting protein. *FEBS Lett.* 568, 30-34 (2004)
49. Ziolkowski, P., Gamian, E., Osiecka, B., Zougman, A. & Wisniewski, J. R. Immunohistochemical and proteomic evaluation of nuclear ubiquitous caesein and cyclin-dependent kinases substrate in invasive ductal carcinoma of the breast. *J. Biomed. Biotechnol.* 2009, 919645 (2009).
50. Zougman, A., Ziolkowski, P., Mann, M. & Wisniewski, J. R. Evidence for insertional RNA editing in humans. *Curr. Biol.* 18, 1760-1765 (2008).
51. Cox, J., et al. A practical guide to the MaxQuant computational platform for SILAC-based quantitative proteomics. *Nat. Protoc.* 4, 698-705 (2009).
52. Cox, J., et al. Andromeda: a peptide search engine integrated into the MaxQuant environment. *J. Proteome Res.* 10, 1794-1805 (2011).
53. Storey, J. D. A direct approach to false discovery rates. *J. Royal Stats. Soc. Series B—Stat. Methodol.* 64, 479-498 (2002).
54. Robin, X., et al. pROC: an open-source package for R and S+ to analyze and compare ROC curves. *BMC Bioinformatics* 12, 77 (2011).
55. Johnston, O., et al. Reduced graft function (with or without dialysis) vs immediate graft function—a comparison of long-term renal allograft survival. *Nephrol. Dial. Transplant.* 21, 2270-2274 (2006).
56. Youden, W. J. Index for rating diagnostic tests. *Cancer* 3, 32-35 (1950).
57. Le Dinh H, Weekers L, Bonvoisin C, et al. Delayed graft function does not harm the future of donation-after-cardiac death in kidney transplantation. *Transplantation Proceedings* 2012; 44: 2795-2802.
58. Nagaraja P, Roberts G W, Stephens M, et al. Influence of delayed graft function and acute rejection on outcomes after kidney transplantation from donors after cardiac death. *Transplantation* 2012; 94: 1218-1223.
59. Singh R P, Farney A C, Rogers J, et al. Kidney transplantation from donation after cardiac death donors: lack of impact of delayed graft function on post-transplant outcomes. *Clinical Transplantation* 2011; 25: 255-264.
60. Brook N R, White S A, Waller J R, et al. Non-heart beating donor kidneys with delayed graft function have superior graft survival compared with conventional heart-beating donor kidneys that develop delayed graft function. *Am J Transplant* 2003; 3: 614-618.
61. Kusaka M, Pratschke J, Wilhelm M J, et al. Activation of inflammatory mediators in rat renal isografts by donor brain death. *Transplantation* 2000; 69: 405-410

The invention claimed is:

1. A method of diagnosing and treating delayed kidney graft function in a human transplant patient, the method comprising:
   i) detecting the level of ACY-1 polypeptide in a blood, serum, or plasma sample isolated from the patient;
   ii) detecting an increased level of ACY-1 in the patient sample compared to a level of ACY-1 in a control sample or a predetermined reference level for ACY-1;
   iii) diagnosing delayed kidney graft function in the patient; and
   iv) treating the patient on the basis of a diagnosis of delayed kidney graft function wherein treating the patient is selected from the group consisting of:
   (a) subjecting the patient to dialysis post transplantation,
   (b) administering intravenous fluid to the patient, and
   (c) administering an immunosuppressant to the patient wherein: the control sample is, or the predetermined reference level is obtained from, a blood, serum, or plasma sample from a healthy subject not having delayed kidney graft function; or the control sample is, or the predetermined reference level is obtained from, a blood, serum, or plasma sample from the patient prior to kidney transplantation.

2. The method of claim 1, wherein the control sample level or predetermined reference level is from a reference database.

3. The method of claim 1, wherein the control sample level or predetermined reference level is obtained from a standard population sample.

* * * * *

SEQUENCE LISTING

```
<160> NUMBER OF SEQ ID NOS: 2

<210> SEQ ID NO 1
<211> LENGTH: 5919
<212> TYPE: DNA
<213> ORGANISM: Homo sapiens

<400> SEQUENCE: 1
ggcggcgctg gccgcggcgg ccgctgcccg gggacgggat ccggatctaa tcctccagta      60
atctcgctga ggcccgaacc agaggcgggc ggggacatcc gcgccgacgc ggccgctggc     120
gccgggacgg ccctcactga cggtcttcgg tctccgcccc gacatccggc ctcggccacg     180
tggtgggcgg accggggcgg tcctgagcct gcgacctcgc aggcgacctc gctggaccct     240
aagtccaggc cacagtcagg gaagggcgct gagaggcgag cgtgagccca gcgacaggag     300
agtgaggtgg gggccctggg gagggataga gggactgggg ctccgtggct tgaaagccgg     360
gcaactggga ggcgttgggg ttttcttgt ttgttttttg tttttgtttt tgcctttttt      420
tttttttagg agggcggggg gagtacaagt ctgggttcaa accttgctca gctactctat     480
gagctgtcct tgaacctctc tgagcctctc agctttctcc tctgtaaagt gggcattctg     540
agcacaaact tcatggggct cttttgggga ttaaataagg aaatgtgctg gaagcagaca     600
gcccagcgcc tgaaacagaa tgggtgctcc ttaatggggg ctccgaaaca cggtatccta     660 ccctgtggg aagtccggga gccgccgtgg ggacaggctg tgtgcaggag ctcaccattt      720
ccagggtctt ggaggggtag ttagccattc actttgcccc cagctcacca cgcgcagcgc     780
catgaccagc aagggtcccg aggaggagca cccatcggtg acgctcttcc gccagtacct     840
gcgtatccgc actgtccagc ccaagcctga ctatggtgag aagacggtgg ttccagagcc     900
```

```
tgtgacgggg cctaagggac ggggactgtg ctctaaacca gcctccaacc cctgtcaccc      960
agctgagccc cactctgctg tcccaaatgg ctccccaacc cctccagcca ttccccaagt     1020
aaatagactg aggcagcccc tccaggttag ggaggaaccc tttccccaga gactctgctg     1080
ctgaccaagg ttactcctgg cagctggtta agaaaaaact tcacctcact ctccagggca     1140
ggagtggtgg gggaagcctg aggcagccac agggaaagga gaggccctcc agaagcccac     1200
tggggctgga caaaggccac agcccttagg gagtcaagct tggtggctag ggcctgggag     1260
gtggctcctg cctgttatcc cagcacttca ggaggttgag gctggcagat tgcttgggcc     1320
caggagttca agactagctt gagcaacatg gcaagactct gtctctacag aaaaaataca     1380
aaaattagtc aggaatggtg gcacacctgt agtcccagct actccagagg ttgaggtggg     1440
aggatcgctt gagcctggga ggttgaggct gcagtgagcc gagatcgcac cacttcactc     1500
ctgccttggt gacagagtga gaccctgtct caaaaaaaaa aaaaaaaaaa ggaaaagaaa     1560
aaaaaaaaac ttagtggctg ggaattgtgt acatgggtcc aaattcctcc tctgtgatta     1620
atcagctgag agatggtggg tgaatctctt catgtctctg tgccatagtt tcccatattt     1680
aaggaagata acaccttcct ccaaccctgt gtccagacat cccctggac ttccagaaag     1740 ggtcactgag tagccaaaaa tatcttcttt cttgggatg gaaatgcaag catctctgag     1800
ggatatggag tgtgtcgggg aggcagcagc ccatttctgg gtatgctcca ctctccgggc     1860
tgcctgggct ggtgggaagc tgtgggtagg cagaagcagc cccaagacac tctgtgcctc     1920
caggagctgc tgtggctttc tttgaggaga cagcccgcca gctgggcctg ggctgtcaga     1980
aagtagaggt gagcctgggg ccctaagcgg ggaagggagg tgggcctggg cacttcctca     2040
ccctgctcag accacctacc ctcctgacca tctccaggtg gcacctggct atgtggtgac     2100
cgtgttgacc tggccaggca ccaaccctac actctcctcc atcttgctca actcccacac     2160
ggatgtggtg cctgtcttca aggtgtgtaa ggggctgggg aggtgggcag tgcaggcctt     2220
ggggacagac atgatgcaga ccccaggatt caacctcaag ttgctcatgg tcctggcccc     2280
agtcctgaca ctaactctca acatccttat gacattacac cactcaagca gccttcatcc     2340
agcagcaagt tctgggccag agtggggtgg ggactggggg gtgggaagca ggagacagca     2400
atgggggatg gcaatcagct gccttcttca gccccgtct ttcctctccc accactccac     2460
ctgtcactcc aacccatgg tgggctccta gggcagggcc actgttgacc agagtggatt     2520
aatggctaaa tttggggttt gggcccctct tcccatccct gcccccagga acattggagt     2580
cacgacccct ttgaggcctt caaggattct gagggctaca tctatgccag gggtgcccag     2640
gacatgaagt gcgtcagcat ccagtgagtg tcctccattc ctactcctcc acaatgtccc     2700
cactggtcca gtggattgaa gcaggacctg agggggtgat tggagaaact caaggccaag     2760
gaacaccgtg acctcttgga caggaactac tgccatgacc attgcatgga tagggagatt     2820
cagaccagag aggggcaggg actttctgga gtccctatca gggtgtggca gggtaaagtc     2880
caggacacag gactccagcc tgctggccct gcctgtgggg ccagcctgcg catctggtgg     2940
ctcccccagc acctggctta tgccccctca ggtacctgga agctgtgagg aggctgaagg     3000
tggagggcca ccggttcccc agaaccatcc acatgacctt tgtgcctggt aggagtggct     3060
cagatacctt tgggaaaggg gagggtgggg cggggcagcc tcctcatctc acgtccctgc     3120
tgcttttaca gatgaggagg ttgggggtca ccaaggcatg gagctgttcg tgcagcggcc     3180
tgagttccac gccctgaggg caggcttgc cctggatgag ggtgagcagg ttggcaagcc     3240
aatgagcagc caggcaggga gtaggaggct gctagtgggg actgagctgc tccacccctct     3300
```

```
gaacccccctt tccctcctca ggcatagcca atcccactga tgccttcact gtcttttata    3360
gtgagcggag tccctggtgt aagtatgagc ttggagggag ggctcactct acaggcggga    3420
ggctaggcca gaaagggcac ggtcctatgc agggttgcac agcaaagttg aggcctgaga    3480
aggccttgaa cccagggcct ctacctccca gctctttcct atctgagctt ctctgagggc    3540
aagccctgaa tgggcagaaa ccagctgtat gctacgggcc ctgagtgggg acaggaccct    3600
gccagaggag cctggaatga gggggagacc tgggcccacc ccaggctgat tgtgtctcca    3660
gcccctcagg ctgaagacac tgccttcccc ctacacctcc cagggggtgc gggttaccag    3720
cactgggagg ccaggccatg cctcacgctt catggaggac acagcagcag agaagctggt    3780
acgtggcacc ccaggaggga gtctgggagt tcaggaggct ctatcctgag ccactgtcc    3840
catttaacct catattctca tagcacaagg ttgtaaactc catcctggca ttccgggaga    3900
aggaatggca gaggtgaggc agcctgggag gcagtggggt ggctctggga ggcggtacca    3960
cagaggatag agtctgagcc acctctttta tctgttgctg ccgctaccct gcccccacac    4020
cacaggctgc agtcaaaccc ccacctgaaa gagggggtccg tgacctccgt gaacctgact    4080
aagctagagg gtggcgtggc ctataacgtg atacctgcca ccatgagcgc cagctttgac    4140
ttccgtgtgg caccggatgt ggacttcaag gtgccacctc cacctgggtt tggaggaggg    4200
atcctgggtc ctcagtcttg tcctagaggc ctctggaaag cctgaaggat cagctcgtct    4260
cccttctctt aggcttttga ggagcagctg cagagctggt gccaggcagc tggcgagggg    4320
gtcaccctag agtttgctca ggtatggact tgggacatgt gatgggagag tgtgggagcc    4380
gggggagacc caagtgtgca acagtggagt gtgtgcttgg tgtgtctgca tatgtctggg    4440
catttctttta tctgtgacag acacatttta ttccaacaag cattcattgt agaggccact    4500
gtgggtgctg gggaatgctg tggggagtaa aattaggcac agttcatgcc cttgtatggt    4560
gaaacgggga gatataaatc aaacatttat gtgatattac ttttttctga gagaatctca    4620
ctccgtcacc caggctgcag tgcagtggca caatctcggc tcacctccgc ctcccgggtt    4680
caagcaattc ttgtgcctca gcctccagag tagttgggat tacaggcacc tgccaccacg    4740
cccagctaat ttttgcattt ttagtagaga cagtgtttca ccatgttggc caggcttgtc    4800
tcgaactcct ggcctcaagt gatccaccca ccttggcctc gcaaaatgct gggattacag    4860
gcatgagcca ctgcgcccag ccgtactttc atataaccca tgtggtacag gaaagggtgg    4920
cccccttgcac tctgaaaacc tgtaactgga gtatccaact agtctgagag gtctggggga    4980
gccatcttga ggaaggggca cttgggctag gatctgaagg atggacagga ggtaagtaga    5040
cggagggtgg gaaggtccca gacctaggac atttgagggg ctgaaagagg acctgtggct    5100
ggactggcta cccagatgtc tgggtaggtg aaggagtggg ggtggggagg tgttatgtac    5160
taggcacagc ccactctatg ggaaataggg caagatgccc aggcccatgt cctgatcctg    5220
ccattcttcc tgtccctcag aagtggatgc acccccaagt gacacctact gatgactcaa    5280
acccttggtg ggcagctttt agccgggtct gcaaggatat gtgagcacgc tggccagctc    5340
tcctcacagc ccagccccct actcctctcc ttcctgctgc cccctccctt ctccctcctt    5400
ctcccacctc tttcccacct tcctttgccc cttcaattct tcgctttctc cctccccatt    5460
catcaggctc tttctcctac aggaacctca ctctggagcc tgagatcatg cctgctgcca    5520
ctgacaaccg ctatatccgc gcggtgagcc acttgcatat agtgcctggg cagtggactg    5580
ggcctgagtg ctggcttttc cctaacggct cttcctcacc cctgcaggtg ggggtccag    5640
ctctaggctt ctcacccatg aaccgcacac ctgtgctgct gcacgaccac gatgaacggc    5700
```

```
tgcatgaggc tgtgttcctc cgtggggtgg acatatatac acgcctgctg cctgcccttg      5760
ccagtgtgcc tgccctgccc agtgacagct gagccctgga actcctaaac ctttgccect      5820 ggggcttcca tcccaaccag tgccaaggac ctcctcttcc cccttccaaa taataaagtc      5880
tatggacagg gctgtctctg aagtactaac acaaggaca                             5919
```

```
<210> SEQ ID NO 2
<211> LENGTH: 408
<212> TYPE: PRT
<213> ORGANISM: Homo sapiens

<400> SEQUENCE: 2

Met Thr Ser Lys Gly Pro Glu Glu His Pro Ser Val Thr Leu Phe
1               5                   10                  15

Arg Gln Tyr Leu Arg Ile Arg Thr Val Gln Pro Lys Pro Asp Tyr Gly
            20                  25                  30

Ala Ala Val Ala Phe Phe Glu Glu Thr Ala Arg Gln Leu Gly Leu Gly
        35                  40                  45

Cys Gln Lys Val Glu Val Ala Pro Gly Tyr Val Val Thr Val Leu Thr
    50                  55                  60

Trp Pro Gly Thr Asn Pro Thr Leu Ser Ser Ile Leu Leu Asn Ser His
65                  70                  75                  80

Thr Asp Val Val Pro Val Phe Lys Glu His Trp Ser His Asp Pro Phe
                85                  90                  95

Glu Ala Phe Lys Asp Ser Glu Gly Tyr Ile Tyr Ala Arg Gly Ala Gln
            100                 105                 110

Asp Met Lys Cys Val Ser Ile Gln Tyr Leu Glu Ala Val Arg Arg Leu
        115                 120                 125

Lys Val Glu Gly His Arg Phe Pro Arg Thr Ile His Met Thr Phe Val
    130                 135                 140

Pro Asp Glu Glu Val Gly Gly His Gln Gly Met Glu Leu Phe Val Gln
145                 150                 155                 160

Arg Pro Glu Phe His Ala Leu Arg Ala Gly Phe Ala Leu Asp Glu Gly
                165                 170                 175

Ile Ala Asn Pro Thr Asp Ala Phe Thr Val Phe Tyr Ser Glu Arg Ser
            180                 185                 190

Pro Trp Trp Val Arg Val Thr Ser Thr Gly Arg Pro Gly His Ala Ser
        195                 200                 205

Arg Phe Met Glu Asp Thr Ala Ala Glu Lys Leu His Lys Val Val Asn
    210                 215                 220

Ser Ile Leu Ala Phe Arg Glu Lys Glu Trp Gln Arg Leu Gln Ser Asn
225                 230                 235                 240

Pro His Leu Lys Glu Gly Ser Val Thr Ser Val Asn Leu Thr Lys Leu
                245                 250                 255

Glu Gly Gly Val Ala Tyr Asn Val Ile Pro Ala Thr Met Ser Ala Ser
            260                 265                 270

Phe Asp Phe Arg Val Ala Pro Asp Val Asp Phe Lys Ala Phe Glu Glu
        275                 280                 285

Gln Leu Gln Ser Trp Cys Gln Ala Ala Gly Glu Gly Val Thr Leu Glu
    290                 295                 300

Phe Ala Gln Lys Trp Met His Pro Gln Val Thr Pro Thr Asp Asp Ser
305                 310                 315                 320

Asn Pro Trp Trp Ala Ala Phe Ser Arg Val Cys Lys Asp Met Asn Leu
                325                 330                 335
```

-continued

```
Thr Leu Glu Pro Glu Ile Met Pro Ala Ala Thr Asp Asn Arg Tyr Ile
            340                 345                 350

Arg Ala Val Gly Val Pro Ala Leu Gly Phe Ser Pro Met Asn Arg Thr
        355                 360                 365

Pro Val Leu Leu His Asp His Asp Glu Arg Leu His Glu Ala Val Phe
    370                 375                 380

Leu Arg Gly Val Asp Ile Tyr Thr Arg Leu Leu Pro Ala Leu Ala Ser
385                 390                 395                 400

Val Pro Ala Leu Pro Ser Asp Ser
                405
```